(12) United States Patent
Ray et al.

(10) Patent No.: US 10,398,587 B2
(45) Date of Patent: Sep. 3, 2019

(54) BREATHING MASK

(71) Applicant: Hupnos, Inc., Alamo, CA (US)

(72) Inventors: Curtis Ray, Alamo, CA (US); Michael Ray, Pleasanton, CA (US); Robert Ray, San Francisco, CA (US)

(73) Assignee: Hupnos, Inc., Alamo, CA (US)

( * ) Notice: Subject to any disclaimer, the term of this patent is extended or adjusted under 35 U.S.C. 154(b) by 0 days.

(21) Appl. No.: 15/729,509

(22) Filed: Oct. 10, 2017

(65) Prior Publication Data
US 2018/0125700 A1    May 10, 2018

Related U.S. Application Data

(60) Provisional application No. 62/406,391, filed on Oct. 10, 2016.

(51) Int. Cl.
*A61F 5/56* (2006.01)
*A61M 16/20* (2006.01)
(Continued)

(52) U.S. Cl.
CPC .................. *A61F 5/56* (2013.01); *A61F 9/04* (2013.01); *A61M 16/024* (2017.08);
(Continued)

(58) Field of Classification Search
CPC . A61F 5/56; A61F 9/04; A61M 16/20; A61M 16/024; A61M 16/202; A61M 16/205; A61M 16/208; A61M 16/209; A61M 16/026; A61M 16/0627; A61M 16/0666; A61M 16/0672; A61M 16/0677; A61M 21/00; A61M 16/06;
(Continued)

(56) References Cited

U.S. PATENT DOCUMENTS 5,474,060 A    12/1995  Evans
5,682,879 A *  11/1997  Bowers .............. A41D 13/1115
                                                128/201.12
(Continued)

FOREIGN PATENT DOCUMENTS

WO        1994022517 A1    10/1994

*Primary Examiner* — Kari K Rodriquez
*Assistant Examiner* — Camtu T Nguyen
(74) *Attorney, Agent, or Firm* — Run8 Patent Group, LLC; Peter Miller

(57) ABSTRACT

One variation of a method—for controlling a breathing mask comprising a flow control module configured to mate to nostrils of a user and comprising an actuator configured to adjust obstruction to airflow out of the flow control module—includes: accessing a wake alarm time; accessing a sleep delay duration; at a first time, receiving an indicator that the user is preparing for sleep; in response to receiving the indicator, triggering the actuator to transition from a minimum-restriction position toward a maximum-restriction position at a second time succeeding the first time by the sleep delay duration, the actuator minimally obstructing airflow out of outlet port in the minimum-restriction position and maximally obstructing airflow out of outlet port in the maximally-restriction position; and, prior to the wake alarm time, triggering the actuator to transition back to the minimum-restriction position.

20 Claims, 7 Drawing Sheets

(51) Int. Cl.
*A61M 16/00* (2006.01)
*A61F 9/04* (2006.01)
*A61M 16/06* (2006.01)
*A61M 21/00* (2006.01)
*A61B 5/00* (2006.01)

(52) U.S. Cl.
CPC ...... *A61M 16/0666* (2013.01); *A61M 16/202* (2014.02); *A61M 16/209* (2014.02); *A61M 21/00* (2013.01); *A61B 5/4809* (2013.01); *A61M 2021/0022* (2013.01); *A61M 2021/0083* (2013.01); *A61M 2205/3303* (2013.01); *A61M 2205/3375* (2013.01); *A61M 2205/3592* (2013.01); *A61M 2230/63* (2013.01)

(58) Field of Classification Search
CPC .. A61M 2021/0022; A61M 2021/0083; A61M 2205/3303; A61M 2205/3375; A61M 2205/3592; A61M 2230/63; A61B 5/48; A61B 5/4806; A61B 5/4809; A61B 5/4818; A61B 5/4812; A61B 5/4815; A62B 23/06

See application file for complete search history.

(56) References Cited

U.S. PATENT DOCUMENTS

| | | |
|---|---|---|
| 8,517,017 B2 | 8/2013 | Bowditch et al. |
| 8,573,219 B2 | 11/2013 | Wondka |
| 8,833,371 B2 | 9/2014 | Kwok et al. |
| 2005/0027207 A1 | 2/2005 | Westbrook et al. |
| 2008/0264422 A1 | 10/2008 | Fishman |
| 2010/0252042 A1 | 10/2010 | Kapust et al. |
| 2011/0259331 A1* | 10/2011 | Witt .................. A61M 16/0666 128/204.18 |
| 2013/0319417 A1 | 12/2013 | Weinman |
| 2014/0251334 A1 | 9/2014 | Kramer |
| 2015/0313535 A1 | 11/2015 | Alshaer et al. |
| 2016/0287829 A1 | 10/2016 | Whitehead et al. |

* cited by examiner

BREATHING MASK

CROSS-REFERENCE TO RELATED APPLICATIONS

This Application claims the benefit of U.S. Provisional Application No. 62/406,391, filed on 10 Oct. 2016, which is incorporated in its entirety by this reference.

TECHNICAL FIELD

This invention relates generally to the field of sleep paraphernalia and more specifically to a new and useful breathing mask and method for reducing snoring in the field of sleep paraphernalia.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Breathing Mask

Figure 1:
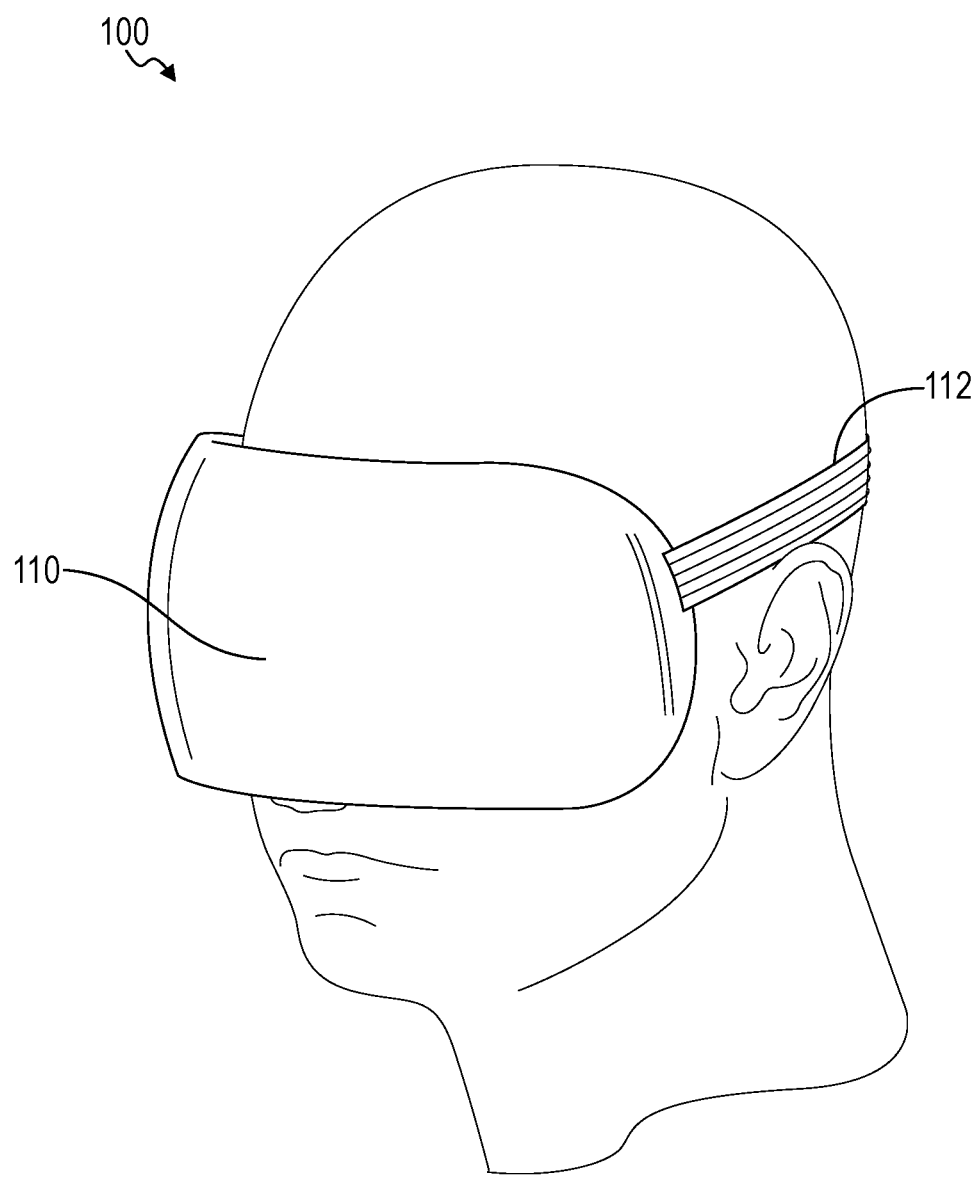
FIG. 1 is a schematic representation of a breathing mask.
Figure 2:
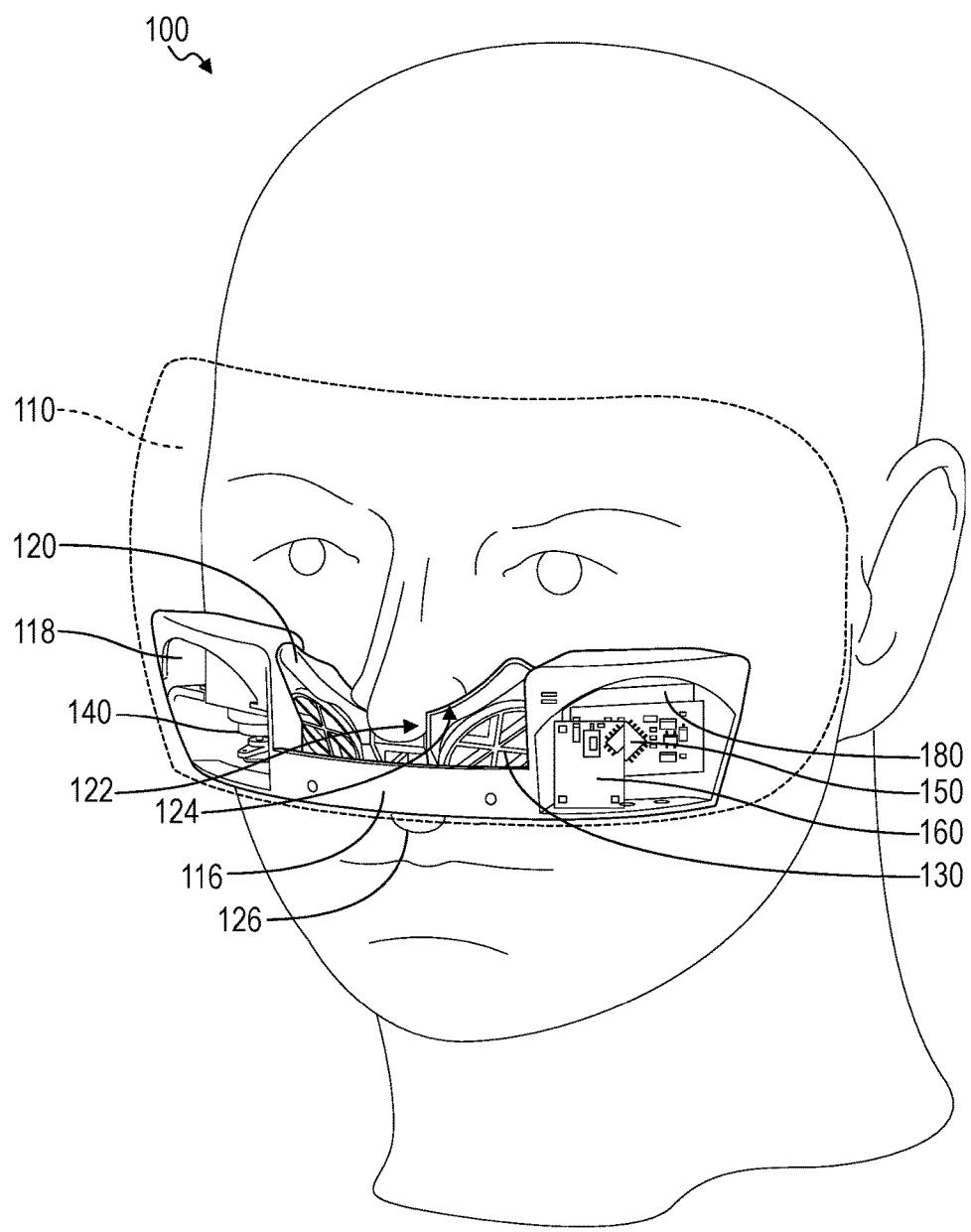
FIG. 2 is a schematic representation of one variation of the breathing mask.

As shown in FIGS. 1 and 2, a breathing mask 100 includes: an eye covering 110 including an opaque material, defining an eye region configured to extend over the eyes of a user wearing the eye covering 110, and defining a nose region configured to extend over the nose of the user; a strap 112 configured to constrain the eye covering 110 on the head of the user; a flow control module 120 coupled to the nose region of the eye covering 110, configured to mate with the nose of the user, including an inlet check valve 130, and including an outlet port 126; an actuator 140 operable over a range of positions between a minimum-restriction position and a maximum-restriction position, coupled to the flow control module 120, and configured to increase constriction of the outlet port 126 from the minimum-restriction position to the maximum-restriction position; and a controller 150 configured to trigger the actuator 140 to transition from the minimum-restriction position toward the maximum-restriction position in response to transition of the user from a wakeful state to a sleep state.

One variation of the breathing mask 100 includes: an eye covering 110 including an opaque material, defining an eye region configured to extend over both eyes of a user wearing the eye covering 110, and defining a nose region configured to extend over a nose of the user; a strap 112 configured to retain the eye covering 110 on a head of the user with the eye region over both eyes of the user and with the nose region aligned to the nose of the user; a flow control module 120 coupled to the nose region of the eye covering 110, defining a manifold 122, including a nostril junction 124 fluidly coupled to the manifold 122 and configured to mate with nostrils of the nose of the user, and including an outlet port 126 fluidly coupled to the manifold 122; an inlet check valve 130 fluidly coupled to the manifold 122 and configured to open in response to a decrease in air pressure inside the manifold 122; an actuator 140 operable over a range of positions between a minimum-restriction position and a maximum-restriction position, the actuator 140 permitting airflow out of the outlet port 126 in the minimum-restriction position and restricting airflow out of the outlet port 126 in the maximum-restriction position; and a controller 150 configured to trigger the actuator 140 to transition from the minimum-restriction position toward the maximum-restriction position in response to transition of the user from a wakeful state to a sleep state.

2. Applications

Generally, the breathing mask 100 can be worn by a user while sleeping and functions to restrict flow of exhaled air out of the user's nose, thereby increasing pressure within the user's airway during exhalation, which may reduce snoring by the user. In particular, increased air pressure within the user's airway during exhalation may cause tissue along the user's airway to stiffen, may open the user's throat, and may stabilize the user's upper airway, thereby reducing the user's tendency to snore. Furthermore, elevated air pressure in the user's airway during exhalation may cause the user's lungs to enlarge, thereby increasing residual volume, extending exhalation time, and steadying the user's breathing, all of which may reduce the frequency and severity of snoring by the user.

The breathing mask 100 includes a flow control module 120 including: a manifold 122 (e.g., an internal volume); a nostril interface configured to mate with the user's nose and fluidly coupled to the manifold 122; a one-way inlet (or "inlet check valve 130") configured to pass air into the manifold 122 when the user inhales; and an outlet port 126 that, when constricted or closed by the actuator 140, restricts airflow out of the manifold 122 when the user exhales. Alternatively, the flow control module 120 can include a pressure relief valve or pressure regulator arranged across the outlet port 126 and configured to permit exhalation through the outlet port 126 while pressure in the user's airway stays above a threshold pressure controlled by the position of the actuator 140, thereby maintaining pressure within the user's airway above the threshold pressure.

The breathing mask 100 can therefore restrict the user's breathing, which may cause the user discomfort while awake. Therefore, the breathing mask 100 further includes a controller 150 that predicts when the user is asleep, determines when the user is asleep, or determines when the user is snoring and selectively restricts airflow through the flow control module 120—by varying the position of the actuator 140—only when such restriction is necessary to reduce the user's snoring and/or is minimally invasive to the user's comfort. (The breathing mask 100 can additionally or alternatively include a wireless communication module 160 configured to wirelessly connect to a local computing device, such as the user's smartphone, executing a native application or other software program that functions as a virtual controller 150 and that remotely executes these processes to calculate positions of the actuator 140.)

Furthermore, a human may exhibit a tendency: to breathe through his nose if he fell asleep while breathing through his nose; and to breathe through his mouth if he fell asleep while breathing through his mouth. To preserve control of the user's breathing through the flow control module 120—in contact with the user's nose—while the user is asleep, the breathing mask 100 minimally obstructs airflow through the user's nose while the user is awake and only begins to constrict airflow during the user's exhalations once the user is determined or predicted to be asleep. In particular, by enabling substantially free airflow through the flow control module 120 when the user is awake, the breathing mask 100 can enable the user to fall asleep under more normal, more comfortable conditions, which may enable the user to fall asleep and remain asleep breathing through his nose. The breathing mask 100 can then restrict the user's exhalations by modifying the flow control module 120 in order to directly address the user's breathing needs while the user is asleep and therefore less sensitive to such flow restrictions, such as when the user is determined to be asleep, is predicted to be asleep, or is determined to be snoring.

The breathing mask 100 integrates the flow control module 120, actuator 140, and controller 150 within an eye covering 110, which defines a visually- and tactilely-approachable soft good package for the control module 120, actuator 140, and controller 150. In particular, the breathing mask 100 can include a mask that houses and supports the control module 120, actuator 140, and controller 150 in a package that visually and tactilely approximates an enlarged sleep mask, which may improve the user's sleep by blocking light from reaching the user's eyes, may be reasonably comfortable for the user physically, and may be reasonably comfortable for the user's self image due to ubiquity of sleep masks while performing additional breathing enhancement functions, including selectively restricting exhalation through the nose to stiffen the user's airway and reduce snoring and selectively waking the user to change sleeping positions when determined to occupy a sleeping position that promotes snoring.

3. Mask+Strap

Figure 8:
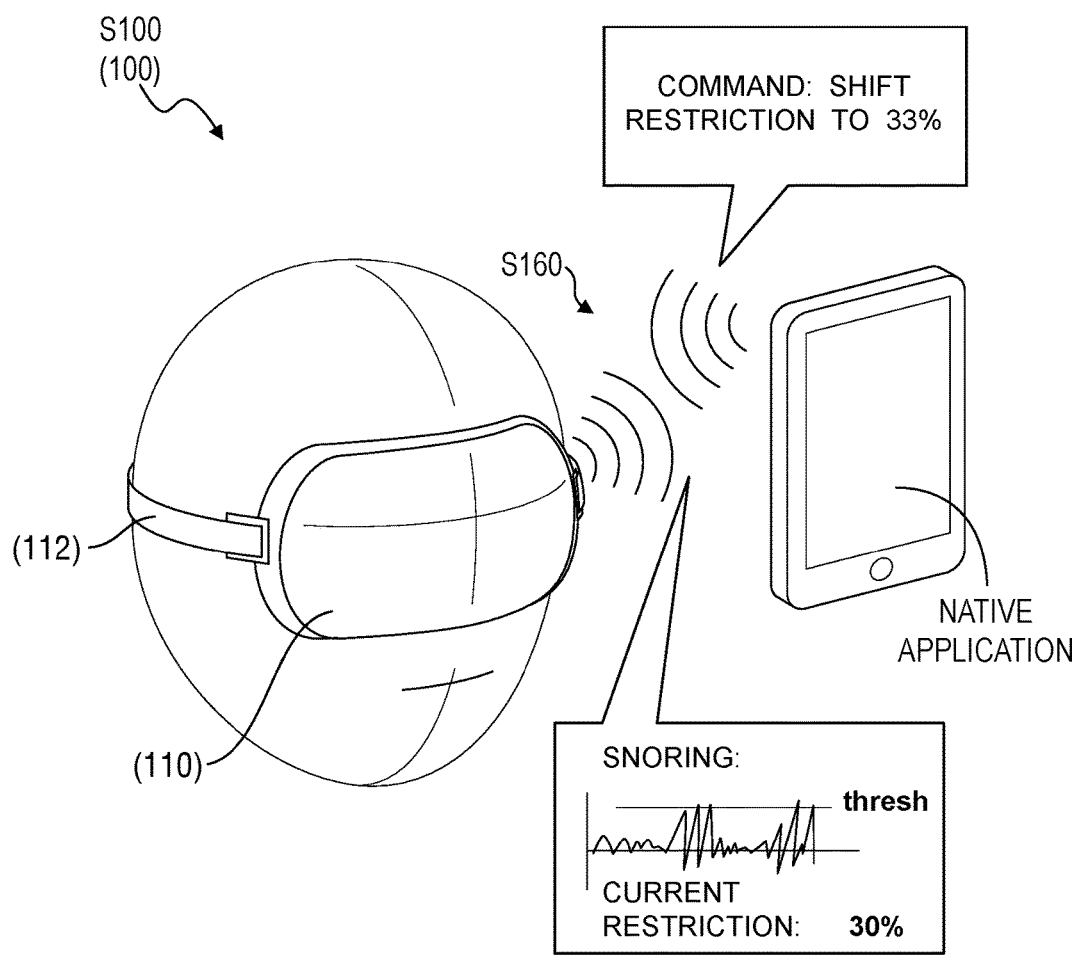
FIG. 8 is a flowchart representation of one variation of the method.

As shown in FIGS. 1 and 8, the breathing mask 100 includes an eye covering 110 that includes an opaque material, defines an eye region configured to extend over both eyes of a user wearing the eye covering 110, and that defines a nose region configured to extend over a nose of the user. The breathing mask 100 can also include a strap 112 configured to retain the eye covering 110 on a head of the user with the eye region over both eyes of the user and with the nose region aligned to the nose of the user. Generally, the eye covering 110 functions as a soft external structure: that conforms to the user's face to comfortably support the flow control module 120 and the actuator 140 (and a battery 180, a wireless communication module 160, etc.) on the user's head; and that covers (i.e., visually obstructs) the flow control module 120, the actuator 140, etc. such that the breathing mask 100 appears as a common sleep mask. The eye covering no can also function to constrain the flow control module 120 against the user's nose in order to achieve some degree of sealing between the nostril junction 124 of the flow control module 120 and the perimeter of the user's external nares.

In one implementation, the eye covering 110 includes a molded or formed opaque (e.g., black) foam structure configured to span a human face from left temple to right temple and from the supraorbital ridge to below the external nares. For example, the eye covering 110 can define a sleep mask including an opaque flexible member forming a convex section configured to deform about a medial axis of the user's head when tensioned against the user's head by the strap 112, thereby conforming the opaque flexible member around the user's face.

In this implementation, the eye covering no can also include a soft textile or foam backing around the perimeter of the opaque foam structure and configured to mate softly against a user's face. For example, the breathing mask 100 can include a contiguous textile cushion 114 or a set of distinct textile cushions 114: arranged about a perimeter of the eye covering no; configured to offset the opaque flexible member from the face of the user (e.g., such that the interior surface of the opaque flexible member is set off from the user's nose); and configured to ventrally align the nostril junction 124 of the flow control module 120 to the user's nostrils. The breathing mask 100 can include a set of textile cushions 114 that can be transiently installed and moved about the perimeter of the eye covering 110, thereby enabling the user to customize the breathing mask 100 to fit his face. For example, these textile cushions 114 can be transiently installed on the eye covering 110 via a hook-and-loop system or via a set of snaps arranged about the perimeter of the eye covering 110.

The strap 112 can include an elastic or adjustable loop extending from opposite sides of the eye covering 110. The strap 112 (or a second strap 112 coupled to the eye covering no) can also be configured to extend below and to restrain the user's jaw or chin, thereby restricting the user's mouth from opening and requiring that the user breathe (predominantly) through his nose rather than through his mouth while the breathing mask 100 is worn.

However, the eye covering 110, the textile cushions 114, and the strap 112 can be of any other materials and define any other form.

4. Flow Restrictor

Figure 3:
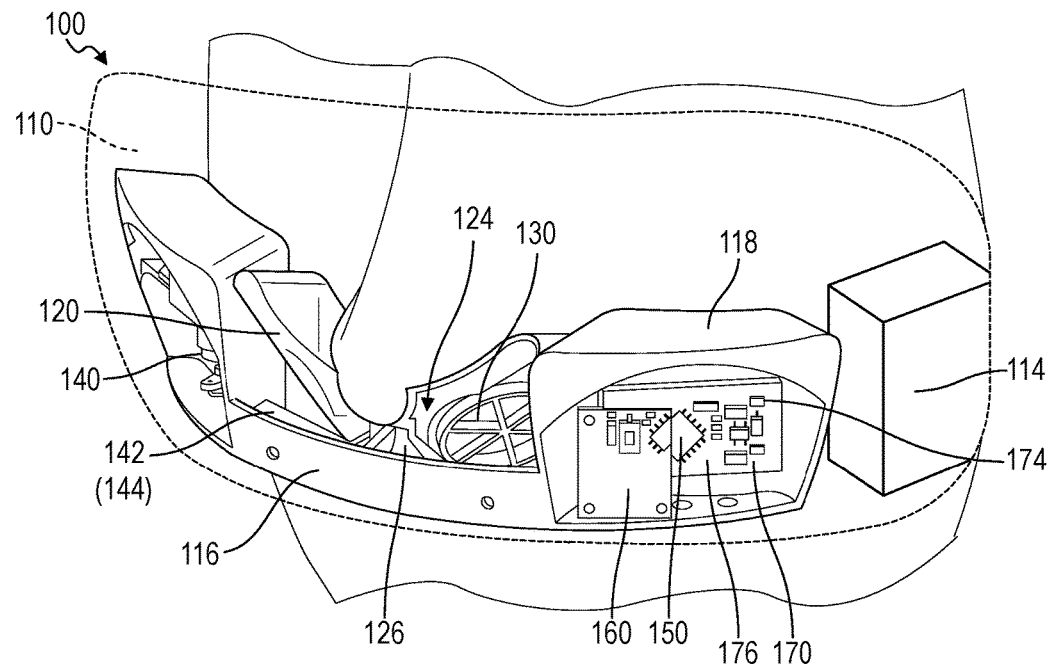
FIG. 3 is a schematic representation of one variation of the breathing mask.
Figure 4:
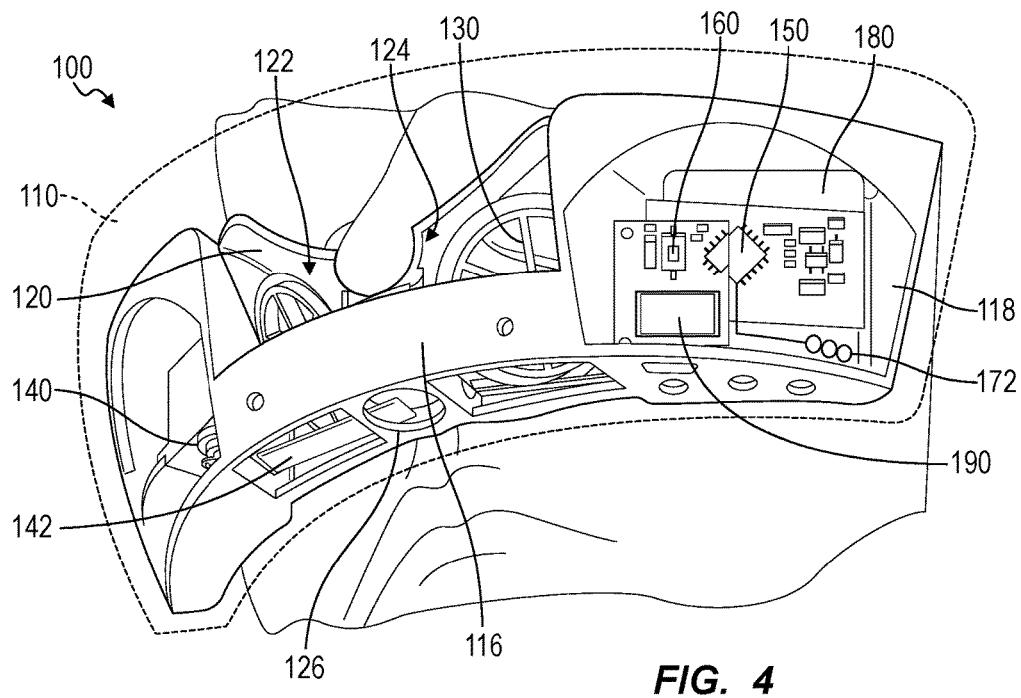
FIG. 4 is a schematic representation of one variation of the breathing mask.

As shown in FIGS. 3 and 4, the breathing mask 100 also includes: a flow control module 120 coupled to the nose region of the eye covering 110, defining a manifold 122, including a nostril junction 124 fluidly coupled to the manifold 122 and configured to mate with nostrils of the nose of the user, and including an outlet port 126 fluidly coupled to the manifold 122; an inlet check valve 130 fluidly coupled to the manifold 122 and configured to open in response to a decrease in air pressure inside the manifold 122; and an actuator 140 operable over a range of positions between a minimum-restriction position and a maximum-restriction position, wherein the actuator 140 minimally restricts airflow out of the outlet port 126 in the minimum-restriction position and maximally restricts airflow out of the outlet port 126 in the maximum-restriction position.

Generally, the flow control module 120 is configured to mate to the nose of a user wearing the breathing mask 100, to permit the user to inhale through his nose with minimal restriction via the inlet check valve(s) 130, and to exhaust air exhaled from the user's nose through the outlet port 126 of variable, controllable cross-sectional area, which may slow the user's rate of exhalation and increase air pressure in the user's airway during exhalation.

4.1 Manifold

Figure 5:
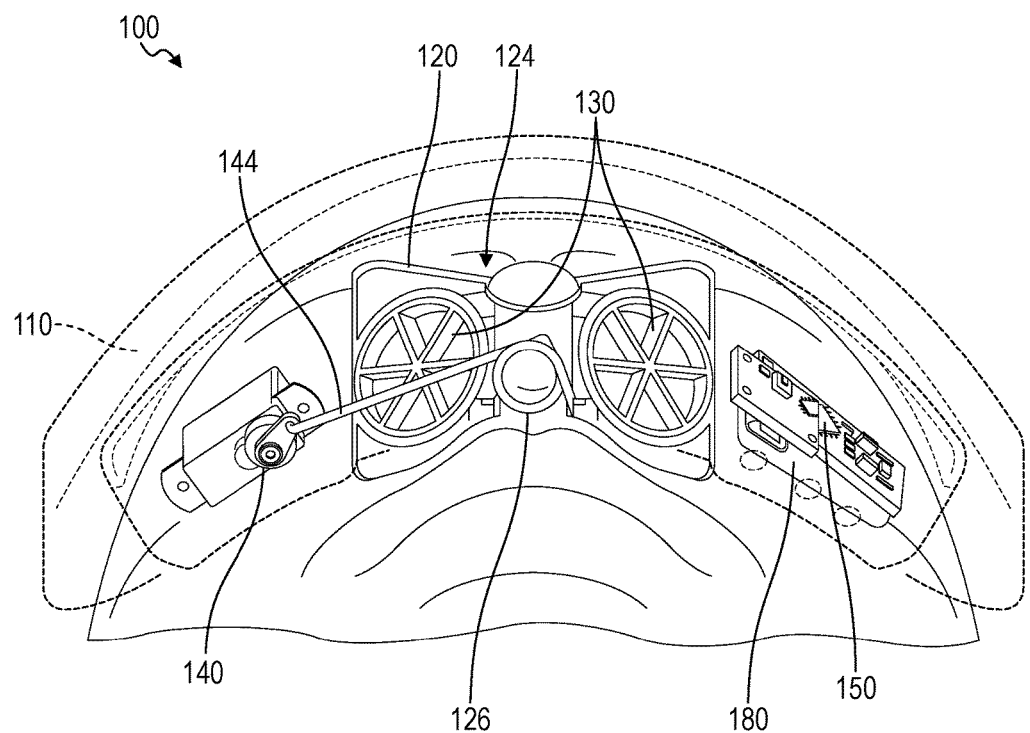
FIG. 5 is a schematic representation of one variation of the breathing mask.

In one variation shown in FIGS. 4 and 5, the flow control module 120 includes: a manifold 122 defining a thin-walled structure forming an internal cavity; a nostril junction 124 configured to mate with and to form a (soft or "loose") seal between the user's nostrils and the manifold 122; and an outlet port 126 fluidly coupled to the manifold 122. The inlet check valve 130 is also fluidly coupled to the manifold 122, is configured to open under negative pressure within the manifold 122 to permit air to enter the manifold 122 when the user inhales, and is configured to close under positive pressure within the manifold 122 when the user exhales, thereby forcing exhaled air to (predominantly) exit the manifold 122 via the outlet port 126. Therefore, in this variation, the flow control module 120 can control (or "enhance") the user's breathing by restricting exhaust of air from the manifold 122 while the user exhales (i.e., during an exhalation cycle in which air pressure inside the manifold 122 increases to exceed ambient).

In one implementation, the flow control module 120 includes a thin-walled polymer structure—such as an injection-molded, blow-molded, or vacuum formed rigid (e.g., nylon) or elastic (e.g., silicone) structure—defining a manifold 122 that fluidly couples the inlet check valve(s) 130, the outlet port 126, and the nostril junction 124.

The nostril junction 124 is configured to contact and to form a (soft or "loose") seal around the user's external nares while the breathing mask 100 is worn by the user, as shown in FIG. 3. In one implementation, the flow control module 120 can define a unitary structure of an elastic material; a top surface of the flow control module 120 can define the nostril junction 124, can include an orifice configured to align to the user's nares, and can be configured to deform around the bottom of the user's nose in order to mate this orifice to a round perimeter of the external nares of the user. For example, the nostril junction 124 can include a soft (e.g., silicone) rib or shoulder extending around a single lozenge orifice or around a pair of circular orifices on the top of the manifold 122. In this example, when compressed against the underside of the user's nose by the eye covering no and strap 112, the nostril junction 124 can deform in order to achieve an approximate seal around the user's external nares while the user inhales and exhales. The nostril junction 124 and the manifold 122 can therefore define a unitary structure. Alternatively, the nostril junction 124 can be overmolded onto the manifold 122 or installed (e.g., adhered, mechanically fastened) over the manifold 122. However, the nostril junction 124 can define any other geometry, can include any other material, and can be configured to engage the user's nose in any other way.

4.2 Inlet Check Valve

The inlet check valve 130 functions to pass air into the flow control module 120 when air pressure inside the manifold 122 drops sufficiently below ambient air pressure during an inhalation cycle. In one implementation, the manifold 122 defines a circular inlet orifice, and the inlet check valve 130 includes a diaphragm arranged over the inlet orifice. In this implementation, the diaphragm can be biased to mate with a seat around the circular inlet orifice in a static position; during an inhalation cycle, decreased pressure in the manifold 122 can lift the diaphragm off of the inlet orifice to permit fresh air to enter the manifold 122 and to pass into the user's nostrils via the nostril junction 124. However, during an exhalation cycle, air exhaled by the user into the nostril junction 124 can increase air pressure within the manifold 122 over ambient air pressure, thereby forcing the diaphragm to close and seal against its seat and forcing air exhaled by the user to exit the manifold 122 through the outlet port 126. (Alternatively, the inlet check valve 130 can include a spring that forces the diaphragm onto or off of its seat in the static position.)

The breathing mask 100 can also include multiple inlet check valves 130 coupled to the flow control module 120, such as one check valve on each side of the vertical centerline (e.g., the medial axis) of the eye covering 110 and straddling the outlet port 126, as described below and shown in FIG. 5. However, the flow control module 120 can include any other number and/or type of inlet check valve 130 configured to permit air to flow into the manifold 122 with minimal pressure loss during user inhalation cycles and to restrict air from flowing out of the manifold 122 during user exhalation cycles.

4.3 Deformable Outlet Port and Actuator

In one implementation shown in FIG. 5: the outlet port 126 includes a tube of an elastic material extending downward from the manifold 122; and the actuator 140 includes a drawbar 144 defining a hook looped around the tube of the outlet port 126 and an electromechanical actuator 140 coupled to the drawbar 144 opposite the hook, configured to retract the drawbar 144 to crush the tube of the outlet port 126 to restrict airflow through the outlet port 126 in the maximum-restriction position, and configured to advance the drawbar 144 to release the tube of the outlet port 126 to permit airflow through the outlet port 126 in the minimum-restriction position.

Generally, in this implementation, the outlet port 126 defines an elastic structure that extends from the manifold 122 and that functions as a pathway through which air exhaled by the user exits the flow control module 120. For example, the manifold 122, nostril junction 124, and outlet port 126 can define a unitary polymer (e.g., silicone) structure. When manipulated by the actuator 140, the elastic outlet port 126 can deform such that its internal orifice area reduces, thereby restricting airflow through the breathing mask 100 during an exhalation cycle. For example, the elastic outlet port 126 can include a silicone tube extending downward from the manifold 122 opposite the nostril junction 124 between two inlet check valves 130, as shown in FIG. 5. The elastic outlet port 126 can also include an internal metallic spring or define a particular geometry configured to return the elastic outlet port 126 to its original undeformed geometry once released by the actuator 140.

In this implementation shown in FIG. 5, the actuator 140 can include a gearhead motor coupled to the elastic outlet port 126 by a drawbar 144 configured to crush the elastic outlet port 126 as the actuator 140 transitions from the minimum-restriction position to the maximum-restriction position. The actuator 140 can be arranged outside of (i.e., remotely from) the flow control module 120, such as within a region of the breathing mask 100 configured to face the user's right cheek (a "right cheek region") when the breathing mask 100 is worn by the user. The actuator 140 can also be coupled to the outlet port 126 by the drawbar 144 or other linkage.

For example, the actuator 140 can include a geared servo motor and a servo arm extending from an output shaft of the servo motor. In this example, a drawbar 144 formed in steel wire can be pivotably coupled to a servo arm on its first end and can define a hook—looped around the elastic outlet port 126—at its second end. When the actuator 140 is held in the minimum-restriction position, the actuator 140 can locate the drawbar 144 in a first position with the hook end of the drawbar 144 released off of the elastic outlet port 126 or only minimally contacting the elastic outlet port 126, thereby limiting distortion of the elastic outlet port 126 by the drawbar 144, maximizing the orifice area of the elastic outlet port 126, and minimizing flow restriction through the elastic outlet port 126. Once the user is determined or predicted to be asleep or once the user is determined to be snoring, the controller 150 can trigger the actuator 140 to advance toward the maximum-restriction position, thereby pulling the drawbar 144 into the elastic outlet port 126. In particular, because the elastic outlet port 126 is of a soft, elastic material, the elastic outlet port 126 can deform (or "crush") when tensioned by the drawbar 144, thereby reducing the orifice area of the elastic outlet port 126 and restricting the flow through the elastic outlet port 126 during an exhalation cycle.

In the foregoing implementation, the effective orifice area (i.e., the cross-sectional area) of the elastic outlet port 126 can lessen proportional to the linear position of the drawbar 144 and therefore proportional to the angular position of the actuator 140. As described below, the controller 150 can actively adjust the position of the actuator 140: to achieve a target flow rate through the soft output orifice; to achieve a target breathing rate; or to achieve a target breathing condition, etc. while the user sleeps, as described below. However, when the controller 150 returns the actuator 140 to the minimum-restriction position to release the drawbar 144 from the elastic output port, the elastic output port can return to its original geometry in which the elastic output port exhibits a maximum orifice area.

In this implementation in which the actuator 140 includes a drawback looped around the outlet port 126 and is configured to selectively crush the outlet port 126 to restrict fluid flow through the outlet port 126, the flow control module 120 can be manually removed from the breathing mask 100 by slipping the elastic outlet port 126 past the drawbar 144 and then drawing the flow control module 120 out of the nose region of the breathing mask 100 (e.g., by removing the elastic outlet port 126 from a receptacle proximal the lower edge of the eye covering no, as described below). Because the actuator 140 is arranged remotely from the flow control module 120, the flow control module 120 can be removed from the breathing mask 100 without removing the actuator 140 or otherwise removing additional elements of the breathing mask 100.

In a similar implementation, the actuator 140 is configured to twist the elastic outlet port 126, thereby deforming the elastic outlet port 126 and reducing the orifice area of the elastic outlet port 126. For example, the flow control module 120 can include a pair of tabs extending from the elastic outlet port 126, each connected to the actuator 140 via a connecting rod; when the controller 150 triggers the actuator 140 to transition from the minimum-restriction position toward the maximum-restriction position, the connecting rods can transfer this rotary motion of the actuator 140 into rotation of the elastic outlet port 126, which can deform under this rotation, thereby reducing its orifice area. In this implementation, the connecting rods can be disconnected from the flow control module 120 to enable the flow control module 120 to be manually removed from the breathing mask 100, such as described above.

In another implementation, the flow control module 120 includes a rigid pocket surrounding the elastic outlet port 126; and the actuator 140 includes an elastic fluid reservoir interposed between the rigid pocket and the elastic outlet port 126 and a pump configured to pump fluid into the fluid reservoir, thereby expanding the elastic fluid reservoir, deforming (e.g., crushing) the elastic outlet port 126, and reducing the orifice area of the elastic outlet port 126. In this implementation, the pump can be arranged remotely from the elastic fluid reservoir and can be coupled to the elastic fluid reservoir via a flexible tube; and the pump, elastic fluid reservoir, and tube can form a closed fluid system with the breathing mask 100. To remove the flow control module 120 from the breathing mask 100—such as for cleaning or replacement, as described above—the elastic fluid reservoir can be removed from the rigid pocket, and the flow control module 120 then drawn out of the breathing mask 100 without removing the pump or opening the fluid system.

In this variation, the manifold 122, nostril junction 124, check valve seats, and outlet port 126 can form a unitary structure, such as a molded thin-walled silicone structure. Alternatively, the manifold 122 can include a rigid structure with soft inserts or overmolded structures defining the nostril junction 124, inlet check valves 130 or check valve seats, and the outlet port 126. For example: the manifold 122 can include a nylon injection-molded or blow-molded thin-walled structure; a silicone tube can be mounted to and extend outwardly from the bottom of the rigid manifold 122 to form the elastic outlet port 126; and a silicone structure overmolded across the top of the rigid manifold 122 can define the nose junction configured to interface the user's nose to the rigid manifold 122.

4.4 Shroud

Figure 6:
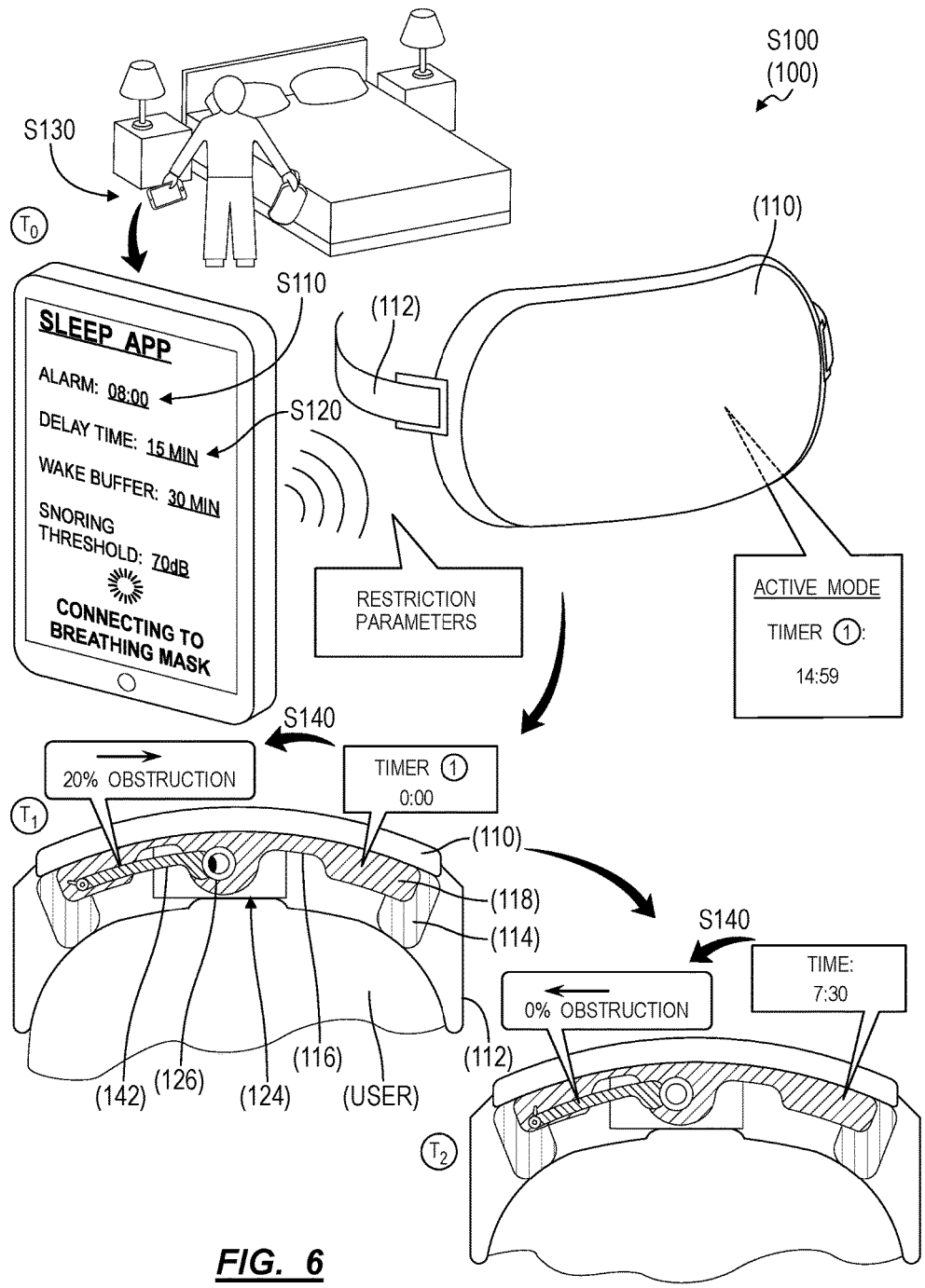
FIG. 6 is a flowchart representation of a method.

In another implementation shown in FIGS. 4 and 6, the actuator 140 further includes a shroud 142 (e.g., a "flapper") adjacent the outlet port 126; and the actuator 140 is coupled to the shroud 142 and is configured to retract the shroud 142 from the outlet port 126 into the minimum-restriction position and to advance the shroud 142 across the outlet port 126 in the maximum-restriction position. In this implementation, the actuator 140 is configured to advance and retract the shroud 142 across the outlet port 126 in order to increase and decrease airflow through the outlet port 126, respectively. For example, the shroud 142 can include a solid elongated member configured to translate linearly along a guide defined about the perimeter of the outlet port 126 and extending from the guide back to a crank arm on the actuator 140. In this example, the actuator 140 can drive the crank arm forward to linearly advance the shroud 142 forward along the guide and across the outlet port 126, thereby obstructing airflow through the outlet port 126. Similarly, the actuator 140 can drive the crank arm in a reverse direction to linearly retract the shroud 142 from the outlet port 126, thereby reducing obstruction to airflow through the outlet port 126. In this example, the actuator 140 can be arranged remotely from the outlet port 126; the user can draw the shroud 142 out of the guide to separate the shroud 142 from the flow control module 120 when removing the flow control module 120 from the eye covering no and can reinsert the shroud 142 into the guide when reassembling the flow control module 120 on the eye covering no.

In another example, the flow control module 120 includes a mechanical iris arranged across the outlet and mechanically coupled to the actuator 140, such as via a connecting rod. In this example, the controller 150 can transition the actuator 140 from the minimum-restriction position to the maximum-restriction position to close the mechanical iris, thereby restricting flow through the outlet during an exhalation cycle. As in the foregoing example, the actuator 140 can be arranged remotely from the mechanical iris and connected to the mechanical iris via a connecting rod. To remove the flow control module 120 from the eye covering 110, the user can disconnect the connecting rod from the mechanical iris before extracting the flow control module 120 from the breathing mask 100.

However, in this variation, the outlet port 126 can include any elastic or rigid structure defining an internal orifice, and the actuator 140 can function in any other way to control an effective cross-sectional area of the outlet port 126. Furthermore, the actuator 140 can include an electromechanical actuator 140 of any other form or type.

5. Pressure Regulator

In another variation, the breathing mask 100 further includes a pressure relief valve arranged across the outlet port 126 and configured to open in response to an air pressure inside the manifold 122 exceeding a trigger pressure; and the actuator 140 is coupled to the pressure relief valve and is configured to set the trigger pressure of the pressure relief valve at a minimum pressure in the minimum-restriction position and set the trigger pressure of the pressure relief valve at a maximum pressure in the maximum-restriction position (e.g., by adjusting a tension on the pressure relief valve). Generally, in this variation, the pressure relief valve enhances the user's breathing by compelling a minimum air pressure—greater than ambient air pressure—inside the flow control module 120 during exhalation cycles, and the actuator 140 selectively adjusts the pressure relief valve in order to set this minimum air pressure between a minimum (e.g., ambient) air pressure and a maximum air pressure.

In one implementation, the pressure relief valve includes a diaphragm: arranged across the outlet port 126; configured to lift from its seat around the outlet port 126 in the presence of a pressure inside the manifold 122 that exceeds ambient air pressure outside the manifold 122 by more than a threshold pressure difference set by the actuator 140 (i.e., during an exhalation cycle); and configured to seal against the seat when pressure within the manifold 122 drops below this threshold pressure difference from ambient air pressure. In this variation, the flow control module 120 can also include a spring element configured to compress the diaphragm against the seat; and the actuator 140 can be configured to modify the tension of the spring element on the diaphragm in order to modify the threshold pressure difference at which the diaphragm opens during an exhalation cycle. The diaphragm and the spring element can therefore cooperate to define an adjustable pressure relief valve, and the actuator 140 can modify a trigger pressure of the pressure relief valve.

In the foregoing implementation, the spring element can include a coil spring element coupled to the diaphragm on its first end and compressed against a nut running along a lead screw on its second end. In this implementation, the actuator 140 can include a rotary actuator configured to rotate the lead screw in order: to move the nut toward the diaphragm, thereby compressing the spring and increasing the threshold pressure difference; and to move the nut away from the diaphragm, thereby releasing the spring and decreasing the threshold pressure difference.

Alternatively, the flow control module 120 can include a rigid backing plate offset in front of the diaphragm; and the spring element can include an elastic reservoir arranged between the rigid backing plate and the diaphragm. In this implementation, the actuator 140 can include a pump configured: to pump a compressible fluid into the elastic reservoir to compress the diaphragm against its seat, thereby increasing the threshold fluid pressure; and to pump the compressible fluid out of the elastic reservoir to release the diaphragm from its seat, thereby decreasing the threshold fluid pressure. However, the diaphragm and spring element can define any other form or geometry, and the actuator 140 can selectively tension the spring element against the diaphragm in any other way in order to modify the threshold pressure difference between the manifold 122 and ambient at which the diaphragm lifts off of its seat during an exhalation cycle.

6. Power and Assembly

In one variation shown in FIGS. 3, 4, and 6, the breathing mask 100 includes a rechargeable battery 180 mounted to the eye covering no and configured to power the actuator 140, the controller 150, and the wireless communication module 160. In one implementation, the battery 180 is arranged in a first rigid housing 118 located on a first lateral side (e.g., to the right) of the flow control module 120; the actuator 140 is arranged in a second rigid housing 118 located on a second lateral side (e.g., to the left) of the flow control module 120; and a beam 116 extends across the flow control module 120 (e.g., between the flow control module 120 and the eye covering no), couples the first rigid housing 118 to the second rigid housing 118, and is mounted to the eye covering 110. For example, the first and second rigid housings 118 can each define water-resistant rigid housings 118 configured to house various electrical components of the breathing mask 100, such as the actuator 140, the battery 180, the controller 150, the wireless communication module 160, and/or various sensors (e.g., a microphone 174, a temperature sensor, a pulse oximetry sensor, an electromyography ("EMG") electrode, and/or an electroencephalogram ("EEG") electrode, etc.). In this example, the weight of components distributed across the two housings 118 can be approximately balanced. The housing 118 containing the actuator 140 can seal against a shroud 142, connecting rod, or other linkage extending from the actuator 140 to the flow control module 120, such as with an elastic (e.g., silicone) O-ring interposed between this housing 118 and the linkage or with an elastic sleeve (e.g., a silicone overmold) arranged over the housing 118. Similarly, the housing 118 containing the battery 180 can include a sealable charging port for recharging the battery 180.

The beam 116 can span the housings 118, and the beam 116 and housings 118 can define a unitary structure, such as a rigid molded polymer structure. This structure can be stitched, snapped, or strapped to the interior surface of the eye covering. To accommodate the shape of the user's face, the beam 116 can be configured to preferentially deflect with the eye covering no about the medial axis of the head of the user. For example, the beam 116 can define a high-aspect-ratio rectangular cross-section with the long axis of the cross-section of the beam 116 arranged substantially parallel to the interior surface of the eye covering no and with the short axis of the cross-section of the beam 116 arranged substantially normal to the interior surface of the eye covering 110. In this configuration, the beam 116 can exhibit a lower moment of inertia about its long axis—parallel to the medial axis of the user's head—than its short axis and may therefore deflect with the eye covering 110 about the user's face while maintaining the locations of the housings 118 on each side of the flow control module 120 and against the interior surface of the eye covering 110.

In this implementation shown in FIGS. 4 and 6, the beam 116 can also define a receptacle proximal the lower edge of the eye covering 110 and configured to locate flow control module 120. In one example: the manifold 122 defines an elastic (e.g., silicone) body; the outlet port 126 includes an elastic (e.g., silicone) tube physically coextensive with the elastic body and defines a lip on its distal end opposite the manifold 122; and the receptacle includes an annular bore centered between the two housings 118 and configured to accept and retain the elastic tube behind the lip in order to flexibly couple the flow control module 120 to beam 116 and thus to the eye covering 110. Therefore, the actuator 140, the flow control module 120, the wireless communication module 160, the controller 150, and/or the inlet check valve 130, etc. can be fully contained within the perimeter of the eye covering 110.

Furthermore, in the foregoing example, the elastic tube and the lip of the outlet port 126 can cooperate with the receptacle to locate the flow control module 120 approximately centered along the medial axis of the eye covering 110. However, the outlet port 126 can also deform (e.g., twist, bend, and stretch), pivot within the receptacle, and rotate within the receptacle, thereby enabling the manifold 122 and the nostril junction 124 to shift relative to the beam 116 to accommodate the user's unique physiognomy (e.g., nose position, nose length, etc. relative to a comfortable position of the eye covering 110 on his face) when the user wears the breathing mask 100. Furthermore, in this example, the flow control module 120 can be removed from the breathing mask 100—such as for cleaning or for replacement with an alternate flow control module 120 of a different shape that better fits the user's facial features—by manually extracting the outlet port 126 from the receptacle (e.g., by pulling the lip on the distal end of the outlet port 126 out of the receptacle). The flow control module 120 can also be reinstalled in the breathing mask 100 by manually inserting the outlet port 126 back into the receptacle.

Alternatively, the flow control module 120 and other components of the breathing mask 100 can be mounted directly to the eye covering 110 or to the strap 112. However, components of the breathing mask 100 can be assembled in any other way and in any other materials.

7. Controller

The controller 150 is configured to trigger the actuator 140 to transition from the minimum-restriction position toward the maximum-restriction position in response to transition of the user from a wakeful state to a sleep state (and vice versa). Generally, the controller 150 is configured to calculate a target degree of restriction to exhalation through the outlet port 126 and to move the actuator 140—which is coupled to the outlet port 126—to a corresponding position between the free-flow and maximum-restriction positions. In particular, the controller 150 is configured to increase restriction to exhalation through the outlet port 126 substantially only when the user is determined or predicted to be asleep and/or is determined to be snoring; otherwise, the controller 150 can move the actuator 140 to the minimum-restriction position in order to achieve minimally restricted flow through the outlet port 126, thereby minimizing discomfort to the user while the user is awake, nearly awake, or approaching wakefulness. The controller 150 can therefore calculate and execute various target levels of restriction to airflow through the outlet port 126: responsive to an identified need to enhance the user's breathing (e.g., when the user is sleeping or snoring specifically); and that minimize obstruction to the user's comfort when breathing enhancement is not immediately needed (e.g., when the user is awake, nearly awake, or approaching wakefulness).

Figure 7:
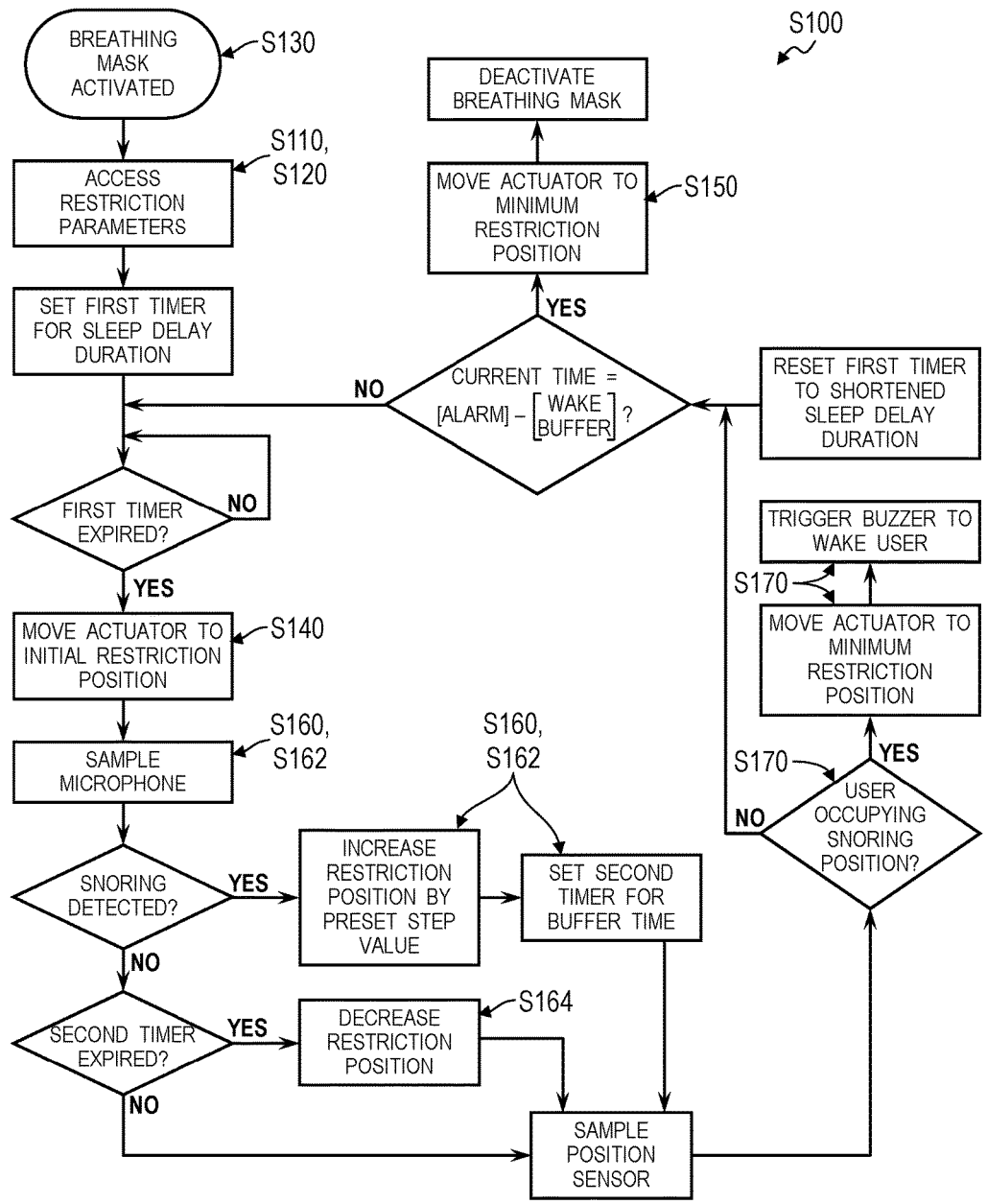
FIG. 7 is a flowchart representation of one variation of the method.

As shown in FIG. 7, the controller 150—integrated into the breathing mask 100 or manifest as a software program executing on an external computing device—can execute a method S100 for controlling the breathing mask 100, including: accessing a wake alarm time in Block S110; accessing a sleep delay duration in Block S120; at a first time, receiving an indicator that the user is preparing for sleep in Block S130; in response to receiving the indicator, triggering the actuator 140 to transition from a minimum-restriction position toward a maximum-restriction position at a second time succeeding the first time by the sleep delay duration in Block S140, wherein the actuator 140 minimally obstructs airflow out of outlet port 126 in the minimum-restriction position and maximally obstructs airflow out of outlet port 126 in the maximally-restriction position; and, prior to the wake alarm time, triggering the actuator 140 to transition back to the minimum-restriction position in Block S150.

7.1 Integrated Controller

In one variation shown in FIG. 2, the controller 150 is arranged within the breathing mask 100, such as arranged in one of the two housings 118 located on each side of the flow control module 120 described above. In this variation, the controller 150 can implement methods and techniques described herein—to calculate target restriction positions for the actuator 140 and outlet port 126—locally at the breathing mask 100.

In this variation, the breathing mask 100 can also include: an analog or digital display (or a buzzer 190, etc.) configured to visually (or audibly, tactilely) communicate a current wake alarm time setting, a current sleep delay duration setting, and/or other settings on the breathing mask Dm; and an input surface through which the user may adjust these settings directly on the breathing mask 100.

Alternatively, the breathing mask 100 can include a wireless communication module 160 configured to communicate wirelessly with an external computing device near the user while the user sleeps. For example, the external computing device can include the user's smartphone or tablet executing a native application through which the user may adjust wake alarm time, sleep delay duration, trigger thresholds for responding to snoring conditions, and/or other settings. In this example, the wireless communication module 160 can wirelessly connect to the user's computing device to synchronize a local timer and to download these settings, which the controller 150 can then implement to locally calculate restriction positions for the actuator 140 and outlet port 126.

In this variation, the breathing mask 100 can also include additional sensors, and the controller 150 can locally recalculate restriction positions for the actuator 140 and outlet port 126 based on outputs of these sensors, as described below. For example, the breathing mask 100 can further include a microphone 174, and the controller 150 can locally calculate a new position for the actuator 140 that increases restriction to airflow through the outlet port 126 when an audio level and/or characteristic of an audio signal detected by the microphone 174 indicates that the user is snoring. In another example, the breathing mask 100 can include an EEG or EMG electrode, a skin temperature sensor, and/or a pulse oximetry sensor configured to contact the user's skin when the breathing mask 100 is worn by the user, and the controller 150 can: locally calculate a degree of wakefulness of the user based on outputs of any one or more of these sensors; shift the actuator 140 toward the maximum restriction position if the user is determined to be in a deeper state of sleep; and shift the actuator 140 toward the minimum restriction position if the user is determined to be in a more wakeful state.

7.2 Remote Controller

In another variation shown in FIG. 8, the controller 150 calculates restriction positions for the actuator 140 and outlet port 126—based on time, sound, position, and/or other sensor streams—remotely from the breathing mask 100 and transmit these restriction positions to the breathing mask 100, such as over an ad hoc wireless network. For example, in this variation, the controller 150 can be manifest as a native application executing on an external computing device (e.g., the user's smartphone or tablet placed on a bedside table near the user's bed) and configured to: monitor time, sound, motion, and/or other local conditions; generate restriction positions; and to transmit these restriction positions to the breathing mask 100. In this example, the breathing mask 100 can include a wireless communication module 160, as described above, that downloads restriction positions from the external computing device for subsequent execution by the actuator 140, as shown in FIG. 8.

In this variation, the native application can leverage sensors integrated into the external computing device, such as a microphone 174 and an accelerometer, to detect snoring and/or physical activity of the user while asleep, respectively. As described above, the breathing mask 100 can also include additional sensors, and the wireless communication module 160 in the breathing mask 100 can transmit data collected from these sensors to the external computing device, such as in real-time or intermittently (e.g., once per one-minute interval). The native application can manipulate these data to remotely calculate new restriction positions for the actuator 140 and outlet port 126 and then return these restriction positions back to the breathing mask 100 for local execution by the actuator 140. The breathing mask 100 can also process, filter, or compress these sensor data locally before uploading a form of these sensor data to the external computing device for processing by the native application.

However, the controller 150 can be manifest as a physical component integrated into the breathing mask 100 and/or as a software program executing on an external device, and the controller 150 can execute methods and techniques described herein locally at the breathing mask 100 and/or remotely at the external computing device to calculate restriction positions for the actuator 140.

7.3 Breathing Mask Activation

In one variation, the breathing mask 100 further includes an activation button or switch; to activate the breathing mask 100 in preparation for bedding down, the user can manually select this button or switch. Alternatively, the breathing mask 100 can include a motion sensor 170, such as an accelerometer, and can transition into the active mode when the breathing mask 100 is disturbed, tapped, or shaken. For example, the breathing mask 100 further includes a motion sensor 170 (e.g., an accelerometer) electrically coupled to the controller 150; and the controller 150 can initiate the timer for the sleep delay duration in response to an output of the motion sensor 170 indicating manipulation of the breathing mask 100 in preparation for use by the user (e.g., when the user is bedding down at night).

Similarly, the breathing mask 100 can include a strain gauge (e.g., a piezoelectric transducer) or other deformation sensor arranged across the eye covering 110; when the user places the breathing mask 100 over his face, which may deform the eye covering 110, the strain gauge can output an electric signal that wakes the controller 150 and/or wireless communication module 160 in the breathing mask 100, thereby transitioning the breathing mask 100 into the active mode. Yet alternatively, the breathing mask 100 can include a temperature sensor, EEG sensor, EMG sensor, or other sensor, as shown in FIG. 3; when an output of any one or more of these sensors changes by a degree sufficient to determine that the breathing mask 100 is being worn by a user, the breathing mask 100 can automatically transition into the active mode.

Upon transitioning into the active mode, the wireless communication module 160 can also broadcast a beacon or other wireless query to connect to the external computing device; and upon receipt of this beacon or wireless query, the external device can automatically wirelessly connect to the breathing mask 100 and can automatically open the native application in order to enable the user to quickly confirm or modify various settings, as described above.

Alternatively, in preparation for bedding down, the user can manually navigate to and open the native application on his smartphone; the smartphone can then broadcast a beacon or other wireless query to connect to the breathing mask 100. Upon receipt of this query, the breathing mask 100 can transition to an active mode and wirelessly connect to the user's smartphone.

However, the breathing mask 100 can transition into the active mode in response to any other input.

7.4 Time

In one implementation shown in FIG. 7, the controller 150: stores a preset sleep delay duration approximating a common duration of transition from a wakeful state to a sleep state for users (e.g., fifteen minutes) or a preset sleep delay duration customized by the user; initiates a timer for the sleep delay duration in response to activation of the breathing mask 100; and then triggers the actuator 140 to transition from the minimum-restriction position to an initial restriction position between the minimum-restriction position and the maximum-restriction position (e.g., from a 0% restriction position to a preset initial restriction position of 20%) in response to conclusion of the timer.

In this implementation, the controller 150 can implement a static preset sleep delay duration to trigger the actuator 140 and can trigger the actuator 140 to restrict airflow through the outlet port 126 at a time that succeeds activation of the breathing mask 100 by this preset sleep delay duration. Alternatively, the user can manually set the sleep delay duration. For example, the user can manually depress a time-decrease (e.g., one-minute decrease) or time-increase (e.g., one-minute increase) button arranged on the breathing mask 100 (e.g., along a bottom edge of the eye covering no) prior to donning the sleeping mask; and the breathing mask 100 can provide visual feedback to the user regarding the duration of the sleep delay duration, such as by flashing a light element (e.g., an LED) adjacent the time-increase and—decrease buttons once per minute of the sleep delay duration. Yet alternatively, the user can access a virtual control panel within the native application executing on his smartphone to manually set the sleep delay duration; once set by the user, the native application can push this sleep delay duration to the breathing mask 100 via the wireless communication module 160, and the breathing mask 100 can implement this sleep delay duration to trigger the actuator 140 to close the outlet port 126 following activation of the breathing mask 100.

In this implementation, the controller 150 can also trigger the actuator 140 to transition back to the minimum restriction position (e.g., a "full-open" position), such as following a preset release time after the breathing mask 100 is activated (e.g., eight hours) or at a time preceding a preset wake alarm time (e.g., 7 AM) by a preset buffer duration (e.g., thirty minutes). For example, for a release time of seven hours, the controller 150 can: initiate a first timer for the sleep delay duration (e.g., fifteen minutes) and a second timer for the release time (e.g., seven hours) once the breathing mask 100 enters the active mode; move the actuator 140 toward the maximum-restriction position (e.g., to an initial actuator 140 position) following expiration of the first timer; and return the actuator 140 to the minimum-restriction position following expiration of the second timer, such as rapidly (e.g., within two seconds) or over a transition period (e.g., over a period of five minutes) in order to limit haptic and audible disturbance to the user.

In the foregoing implementation, the user can set the release time manually, such as at the breathing mask 100 or through the native application as described above. For example, the user can enter a value of eight hours into an expected sleep duration field within the native application. In this example, the native application can then calculate a release time of seven hours by subtracting the current sleep delay duration of fifteen minutes and a waking buffer of 45 minutes (e.g., a time to open the output port prior to the user waking in order to minimize discomfort to the user when transitioning to wakefulness and to accommodate possibility of the user waking prior to activation of his alarm) from the sleep duration of eight hours. The native application can then push this release time to the breathing mask 100 via the wireless communication module 160, and the controller 150 can set and monitor local timers accordingly.

Alternatively, the native application can set and maintain such timers locally on the external computing device paired with the breathing mask 100, and the native application can intermittently wirelessly connect to the breathing mask 100 and transmit commands for the actuator 140 position to the breathing mask 100 for (immediate) execution by the actuator 140.

The native application can also: incorporate a virtual alarm clock; enable the user to set an alarm time at which the virtual alarm triggers actuation of a light element, buzzer 190, and/or speaker—at the external computing device and/or at the breathing mask 100—to wake the user; and automatically transmit a command to the breathing mask 100 to transition the actuator 140 back to the minimum-restriction position at a time preceding the alarm time by the waking buffer (e.g., a static or user-selected waking buffer between fifteen and 60 minutes in length). (Alternatively, the native application can interface with another native virtual alarm clock application executing on the external computing device.) For example, the wireless communication module 160 can receive—from the external computing device—an indicator of an upcoming activation of a wake alarm, set by the user, at the external computing device; and the controller 150 can trigger the actuator 140 to transition back to the minimum-restriction position at a time preceding the upcoming activation of the wake alarm by a preset duration (hereinafter a "waking buffer"). The native application can therefore trigger the controller 150 to return the actuator 140 to the minimum-restriction position in response to a time of day or to a value on a virtual alarm clock, thereby returning the breathing mask 100 to minimally-obstructed airflow through the outlet port 126 before the virtual alarm wakes the user.

Furthermore, when the controller 150 first triggers the actuator 140 to move toward the maximum-restriction position following initial activation of the breathing mask 100, the controller 150 can transition the actuator 140 to an initial restriction position between the minimum- and maximum-restriction positions, such as a preset initial restriction position of 20% or an initial restriction position set by the user or learned by the controller 150 over time. The breathing mask 100 can also include one or more input regions through which the user may shift the initial restriction position toward or away from the minimum-restriction position in order to reduce or increase restriction to airflow during exhalation once the controller 150 predicts that the user is asleep. For example, if the initial restriction position causes breathing discomfort sufficient to wake the user, the user can manually depress a restriction-decrement button on the breathing mask 100 or in the native application to shift the initial restriction position back toward the minimum-restriction position. In this example, upon such adjustment by the user, the controller 150 can: move the actuator 140 back to the minimum-restriction position to minimize resistance to exhalation while the user falls back asleep; reset a timer for the sleep delay duration; and then move the actuator 140 to the new initial restriction position upon expiration of this timer.

The native application can also collect feedback from the user and/or the user's partner regarding whether the user has continued to snore while sleeping with the breathing mask 100; and the native application or the controller 150 can then automatically increase the initial actuator 140 position if such feedback indicates that the user is still snoring at night (and vice versa). For example, if the user's partner notifies the user that he is still snoring, such as the following day as described below, the user can select a restriction-increment button on the breathing mask 100 or in the native application; the controller 150 can then store this new, more aggressive initial restriction position and implement this new initial restriction position when the breathing mask 100 is activated the following night.

Therefore, the wireless communication module 160 can receive—from the external computing device associated with the user—a sleep delay duration, an initial restriction position, and/or other time and restriction parameters from the user's computing device, such as static preset parameters and/or parameters customized by the user at the external computing device.

7.5 Sound and Snoring

In another variation shown in FIGS. 7 and 8, the controller 150 (or the native application) determines that the user is snoring based on sounds (or vibrations) detected near the user. When snoring is detected, the controller 150 can selectively advance the actuator 140 toward the maximum-restriction position, thereby restricting airflow out of the outlet port 126 when the user exhales, which may stiffen the user's airway and thus reduce the user's snoring.

7.6.1 Detecting Snoring

In this variation, the breathing mask 100 can include a microphone 174 (or a throat microphone, a bone microphone, etc.), and the controller 150 can analyze a signal output by the microphone 174 during a sleep period to detect snoring. For example, the controller 150 can locally implement frequency analysis techniques to identify intermittent periods of noise between 200 Hz and 600 HZ occurring at regular intervals of 0.125 Hz in a signal read from the microphone 174, and the controller 150 can correlate these periods of noise with snoring and respond accordingly. The controller 150 can also transmit snoring-related data generated locally at the breathing mask 100 back to the native application—via the wireless communication module 160—for storage, further processing, and/or presentation to the user in a visual format within the native application. The native application can also process these snoring-related data at the external computing device, calculate target actuator 140 positions for the actuator 140, and transmit these target actuator 140 positions to the controller 150 for execution.

Alternatively, the native application can access a signal from a microphone integrated into the external computing device and can implement similar methods and techniques to identify instances of snoring, to calculate target actuator 140 positions responsive to detected snoring, and to send related commands back to the breathing mask 100 for execution. In the foregoing implementations, the controller 150 or native application can implement similar methods and techniques to detect snoring based on outputs of: an accelerometer or vibrometer integrated into the breathing mask 100; an accelerometer or vibrometer integrated into the peripheral device placed on the user's bed or in the user's pillow and wirelessly connected to the external computing device; an accelerometer integrated into the external computing device; or any other noise or vibration sensor integrated into or connected to the breathing mask 100 or computing device.

In one variation, the breathing mask 100 includes two microphones, including: a first microphone arranged proximal the flow control module 120, such as configured to face the user's mouth when the breathing mask 100 is worn by the user in order to detect sounds originating from the user; and a second microphone arranged remotely from the first microphone, such as arranged on the front of and facing outwardly from the eye covering 110 in order to detect ambient sounds. In this variation, the controller 150 can sample the first and second microphones and then: determine that the user is snoring if the amplitude of the signal detected by the first microphone significantly exceeds the amplitude of the signal detected by the second microphone; and determine that the user is not snoring if the amplitude of the signal detected by the second microphone approximates or exceeds the amplitude of the signal detected by the first microphone. Alternatively, the breathing mask 100 can include a first microphone configured to output a signal predominantly representing sounds originating at the user, and the wireless communication module 160 can transmit continuous or intermittent outputs from this first microphone to the external device. In this implementation, the native application can compare the signal values received from the breathing mask 100 to signal values read from a second microphone integrated into the external computer system in order to distinguish sounds originating at the user's airway from ambient sounds (e.g., the user's partner snoring, road noise, fireworks, etc.) according to similar methods.

7.6.2 Closed-Loop Controls

In this variation, the controller 150 (or the native application) can implement closed-loop controls to selectively open and close the outlet port 126 in response to detected snoring and/or based on a duration or intensity of the user's snoring, as shown in FIG. 7. In one example, once the breathing mask 100 is activated, the controller 150 can maintain the actuator 140 in the minimum-restriction position until snoring is detected by the controller 150 (or by the native application executing on a computing device nearby). However, once snoring is detected, the controller 150 (or the native application) can increase the target actuator 140 position—such as by a preset step value of 5% restriction—and then move the actuator 140 to this new target actuator 140 position. If snoring persists after a sampling interval, such as after ten seconds following this first shift in the position of the actuator 140, the controller 150 can again increment the target actuator 140 position, such as by the preset step value to 10% restriction, and move the actuator 140 to this second target actuator 140 position. The controller 150 can repeat this process over time up to the maximum-restriction position (e.g., 100% restriction) until snoring ceases.

In the forgoing example, once the controller 150 determines that snoring has ceased, the controller 150 can initialize a third timer for a relax time, such as a relax time of 60 minutes. In this example, if the controller 150 (or the native application) does not detect snoring prior to expiration of the third timer, the controller 150 can relax the target actuator 140 position toward or fully to the minimum-restriction position and can move the actuator 140 to this relaxed target actuator 140 position. The controller 150 (or the native application) can continue to track sounds and/or vibrations at the breathing mask 100 (or at the external computing device), and the controller 150 can increment the target actuator 140 position back toward the maximum-restriction position and move the actuator 140 accordingly. The controller 150 (or the native application) can therefore implement closed-loop controls to increase and decrease restriction through the outlet port 126 based on whether snoring is detected or not detected, respectively, during operation of the breathing mask 100.

Therefore, in this variation, the method S100 can further include Block S160, which includes: reading a first output of a microphone, proximal the user, at a first time (e.g., succeeding transition of the actuator 140 to the initial restriction position after activation of the breathing mask 100); and triggering the actuator 140 to move from its current position (e.g., the initial restriction position) to a second position in response to characterizing the first output of the microphone as snoring by the user, wherein the second position is defined between the initial restriction position and the maximum-restriction position and is associated with a second degree of obstruction to airflow through the outlet port 126 greater than an initial degree of obstruction at the initial restriction position. In this variation, the method S100 can also include Block S162, which includes: reading a second output of the microphone at a second time succeeding the first time by a preset buffer time (e.g., one minute); and triggering the actuator 140 to move from the second position to a third position in response to characterizing the second output of the microphone as snoring by the user, wherein the third position is defined between the second position and the maximum-restriction position and is associated with a third degree of obstruction to airflow through the outlet port 126 greater than the second degree of obstruction. The method S100 can further include Block S164, which includes: reading a third output of the microphone at a third time succeeding the second time (e.g., by the relax time); and triggering the actuator 140 to move from the fourth position back toward the minimum-restriction position in response to characterizing the third output of the microphone as excluding snoring by the user in order to decrease obstruction to airflow through the outlet port 126.

In this variation, the controller 150 can also upload snoring-related data to the native application over time, and the native application can transform these data into a breathing model for the user or directly into commands to alter the target actuator 140 position. For example, the controller 150 at the breathing mask 100 and the native application at the external computing device can cooperate to track: times of day at which the user snores; lengths of time into a sleep period at which the user begins to snore; snoring period duration; snoring intensity (e.g., based on a loudness of noise recorded by the microphone integrated into the breathing mask 100 or into the user's computing device); ambient conditions (e.g., temperature, barometric pressure, $CO_2$ concentration); and/or a user's sleeping position when snoring and/or not snoring (e.g., based on an output of an accelerometer integrated in the breathing mask 100). The native application can then extrapolate trends from these snoring-related data. For example, the native application can: identify a time of night at which the user is particularly likely to begin snoring from data collected during previous sleep periods; preempt the user's snoring by automatically transmitting a command to the controller 150 to advance the actuator 140 toward the maximum-restriction position in advance of (e.g., fifteen minutes before) the time at which the user is likely to begin snoring; and otherwise prompt the controller 150 to move the actuator 140 to the minimum-restriction position. The native application can similarly extrapolate snoring trends related to ambient conditions from data collected during previous sleep periods and then apply current ambient conditions to these trends to predict a time and/or intensity of snoring by the user during the current sleep period and then calculate a target actuator 140 position accordingly.

7.6.3 Trigger Settings

The controller 150 and/or the native application can maintain various snoring-related triggers to provoke increasing obstruction to airflow through the outlet port 126, as shown in FIGS. 7 and 8. For example, the controller 150 can store: a threshold snoring amplitude, such as in the form of decibels above a baseline or ambient noise level at which the controller 150 will trigger the actuator 140 to increase obstruction to airflow out of the outlet port 126; and/or a threshold snoring duration, such as a period of ten second, 30 seconds, or one minute of continuous snoring that, when detected, triggers the actuator 140 to increase obstruction to airflow out of the outlet port 126.

In this variation, the controller 150 or the native application can implement static snore-related triggers. Alternatively, these triggers can be set directly or influenced by the user or by the user's partner. For example, if the user notices that he is awoken at night by his own snoring or is experiencing poor sleep quality, the user can manually decrease the threshold snoring amplitude and/or the threshold snoring duration through the native application or directly via input regions on the breathing mask 100. Similarly, if the user is experiencing discomfort from restricted exhalation, the user can increase the threshold manually at the native application or at the breathing mask 100.

In another example, the native application (or a remote computer system, such as a remote server or computer network) can regularly (e.g., daily or once per three-day interval) serve prompts to the user's partner—such as in the form of a text message sent to the partner's smartphone—to confirm whether the partner was awoken by the user's snoring or noticed the user snoring during the previous night. If the partner returns a "yes" or equivalent value, the native application (or the remote computer system) can automatically decrease the snoring threshold amplitude and/or snoring threshold duration; if the partner returns a "no," "don't know," or equivalent value, the native application (or the remote computer system) can preserve or increase the snoring threshold amplitude and/or snoring threshold duration. The native application and/or the controller 150 can implement these new snoring thresholds the next time the user uses the breathing mask 100.

In yet another example, a second instance of the native application can be loaded onto the partner's computing device. This second instance of the native application can execute a partner mode and can be linked to the breathing mask 100 and to the first instance of the native application executing on the user's computing device. While the user and the partner have bedded down and the breathing mask 100 is active, if the user is snoring but the snoring threshold amplitude and/or duration have not been met such that the actuator 140 has not moved further toward the maximum restriction position to ameliorate the user's snoring, rather than wake the user to stop his snoring, the partner can open the second instance of the native application on her computing device and select a snoring abatement option. The second instance of the native application can then connect directly to the breathing mask 100 or to the first instance of the native application executing on the user's computing device to trigger the actuator 140 to move further toward the maximum-restriction position. In this example, the controller 150 or the first instance of the native application can also reduce the snoring threshold amplitude and/or duration accordingly. Similarly, the controller 150 or the native application can: record a snoring amplitude via the microphone in the breathing mask 100 or in the user's computing device around the time that the partner submitted this manual confirmation of the user snoring; continue to advance the actuator 140 to increase obstruction to the outlet port 126 until this snoring level drops; and adjust the snoring threshold amplitude accordingly.

However, the controller 150 and/or native application can implement any other methods or techniques to detect, track, and respond to snoring by the user.

8. Sleep Position

As shown in FIG. 7, the controller and/or the native application can also: track sleeping positions for which the user is most likely to snore from snoring-related data collect previously; and then cooperate with the breathing mask 100 to implement target actuator 140 positions that preempt snoring during the current sleep period based on the user's current sleeping position. In one example, if the native application extrapolates a trend from past snoring-related data that suggests that the user snores with greater intensity while lying on his back, a current output of the accelerometer integrated into the breathing mask 100 indicates that the user is currently laying on his back, and sound data does not indicate that the user is currently snoring, the native application can still prompt the controller 150 to move the actuator 140 toward the maximum-restriction position in order to achieve greater restriction to exhalation, thereby preempting snoring while the user is sleeping on his back. In this example, once an output of the accelerometer indicates that the user has rolled to his side, which trends in the user's snoring may indicate is less likely to result in snoring or results in lower-intensity snoring by the user, the controller 150 can automatically trigger the actuator 140 to retract back toward the minimum-restriction position. (The controller 150 can also implement the foregoing methods and techniques locally at the breathing mask 100.)

In the foregoing implementation, if the user is determined to be sleeping in a position associated with snoring or higher-intensity snoring by the user, the controller 150 and/or native application can also trigger a buzzer 190 (e.g., a vibrator) integrated into the breathing mask 100 to wake the user, as shown in FIGS. 4 and 7, thereby waking the user and prompting the user to roll to a sleeping position less likely to lead to snoring or likely to yield less intense snoring. For example, the breathing mask 100 can further include: a buzzer 190 coupled to the eye covering no; and a position sensor 176 configured to output a signal corresponding to an orientation of the eye covering no. In response to an output of the position indicating an orientation of the eye covering 110 that is associated with snoring, the controller 150 can: trigger the actuator 140 to move to the minimum-restriction position in order to limit discomfort to the user when the user is subsequently awoken; and then actuate the buzzer 190 to wake the user. The controller 150 can then: sample the position sensor 176 to confirm that the user has moved to a more appropriate sleeping position; restart a timer for the same sleep delay duration (e.g., fifteen minutes) or a shortened sleep delay duration (e.g., two minutes), since the user may fall asleep relatively quickly; and then trigger the actuator 140 to move toward the maximum restriction position once this timer expires.

In another example, if the controller 150 determines that the user is snoring and occupying a position that exacerbates snoring or correlated with snoring, the controller 150 can selectively: prompt the user to modify his sleeping position by triggering a buzzer 190 integrated into the breathing mask 100 if the user is in a more wakeful state; or trigger the actuator 140 to move toward the maximum restriction position in order to increase exhalation restriction through the outlet port 126 if the user is in a deeper sleep state.

In this implementation, the breathing mask 100 can additionally or alternatively include a light element inside the eye covering 110, such as a set of colored LEDs arranged across the inside of the eye region of the eye covering 110; and the controller 150 can illuminate the light element to wake the user and/or to visually prompt the user to assume an alternate sleeping position.

Therefore, the method S100 can further include Block S170, which includes: reading an output of a position sensor 176 arranged in the breathing mask 100 at a first time following activation of the breathing mask 100; and, in response to the output of the position indicating an orientation of the eye covering 110 that is associated with snoring, triggering the actuator 140 to move to the minimum-restriction position, then actuating a buzzer 190 in the breathing mask 100 to wake the user, and then triggering the actuator 140 to transition from the minimum-restriction position back toward the maximum-restriction position following a shortened sleep delay duration.

However, the controller 150 can implement any other method or techniques to detect the user's position and to prompt the user to change this position in order to reduce snoring.

7.6 Wakefulness

In another variation, the controller 150 (and/or the native application) can vary the position of the actuator 140—and therefore restriction to airflow through the outlet port 126—based on a determined wakefulness state of the user. In particular, the controller 150 (or the native application) can: shift the target actuator 140 position toward the maximum-restriction position or increase a maximum allowable distance from the minimum-restriction position as the user becomes less wakeful; and shift the target actuator 140 position toward the minimum-restriction position or decrease the maximum allowable distance from the minimum-restriction position as the user becomes more wakeful.

In one implementation, the controller 150 (or the native application) can: transform signals output by an accelerometer integrated into the breathing mask 100 into a measure of motion; correlate this level of motion with the user's wakefulness; and then move the actuator 140 directly to a reduced airflow restriction position accordingly. Alternatively, the controller 150 can reduce a maximum allowed airflow restriction through the outlet port 126 when motion is detected at the breathing mask 100, thereby setting a lower upper bound on airflow restriction through the outlet port 126 and limiting a distance that the actuator 140 can travel toward the maximum restriction position, which may limit discomfort to the user if the user wakes soon after this period. If such motion ceases, the controller 150 can then return the maximum allowed airflow restriction back to an original level.

In another implementation, the breathing mask 100 includes an EEG electrode configured to contact the user's skin, such as over the user's forehead at a "G," "FP1," or "FP2" position, and configured to output a signal representing the user's alpha, beta, theta, and/or delta brainwaves. In this implementation, the controller 150 (or the native application) can transform a signal from the EEG sensor into a level of wakefulness or into a wakefulness state of the user. The controller 150 can then implement methods and techniques as described above to vary the position of the actuator 140 or the maximum allowable airflow restriction through the outlet port 126 based on the determined level of wakefulness or the determined wakefulness state of the user.

Similarly, the breathing mask 100 can include a biometric sensor 172—such as an EEG, EMG, skin temperature, or pulse oximetry sensor—arranged on the eye covering no, configured to contact the user's skin when the breathing mask 100 is worn, and electrically coupled to the controller 150. In this implementation, the controller 150 can: read outputs of the biometric sensor 172; interpret a first change in an output of the biometric sensor 172 over a first period of time as transition of the user from the wakeful state to the sleep state over the first period of time; trigger the actuator 140 to transition from the minimum-restriction position toward the maximum-restriction position over a first transition period succeeding the first period of time in response to detecting transition of the user from the wakeful state to the sleep state; interpret a second change in the output of the biometric sensor 172 over a second time succeeding the first period of time as transition of the user from the sleep state to the wakeful state over the second period of time; and trigger the actuator 140 to transition back to the minimum-restriction position over a second transition period in response to detecting transition of the user from the sleep state to the wakeful state. The controller 150 can similarly merge outputs of multiple biometric, motion, sound, and/or other sensors in the breathing mask 100 into a prediction of the wakefulness of the user and adjust the position of the actuator 140 accordingly.

The breathing mask 100 and native application can also cooperate to collect sleep, motion, snoring, and airflow restriction data related to the user over time. A remote computer system can: aggregate such data from the breathing mask 100 and other units of like breathing masks; extrapolate trends from these data; generate or revise airflow restriction models based on user demographic, snoring frequency, snoring amplitude, time of day, sleep cycle, sleeping position, etc.; and push these new or revised airflow restriction models back the breathing mask 100 and/or native application for execution to control the position of the actuator 140 while the user is sleeping.

9. Sleep Quality

In one variation, the controller 150 selectively opens and closes the outlet port 126 in order to control a $CO_2$ concentration in a volume of air inhaled by the user during an inhalation. Generally, $CO_2$ may function as a respiratory stimulant; elevated concentrations of inspired $CO_2$, such as between 2% and 3% molar concentrations, may increase total sleep and decrease sleep latency (i.e., time to falling asleep) for humans, while $CO_2$ concentrations outside of this range may decrease sleepiness. In this variation, the controller 150 can manipulate the outlet port 126 to achieve a target concentration of $CO_2$ inhaled by the user.

In one implementation in which the flow control module 120 includes a pressure relief valve, the breathing mask 100 includes a $CO_2$ concentration sensor configured to output a signal corresponding to a $CO_2$ concentration in exhaled air. In this implementation, the controller 150 can sample the $CO_2$ concentration sensor and can increase the trigger pressure of the pressure relief valve if the measured $CO_2$ concentration of exhaled air is less than a threshold $CO_2$ concentration (e.g., less than 2%) or falls outside of a target range of $CO_2$ concentrations (e.g., 2% to 3%), thereby increasing a pressure within the user's airway at which the pressure relief valve closed and increasing a total volume of air—and therefore residual $CO_2$—remaining in the user's lungs upon completion of the exhalation cycle. When the user inhales during a next inhalation cycle, fresh air containing a lower concentration of $CO_2$ can mix with air in the user's lungs at a higher concentration (e.g., 5%) to achieve a total $CO_2$ concentration between 2% and 3% for air in the user's lungs for the inhalation.

In another implementation, the manifold 122 of the flow control module 120 (or the enclosed volume between the interior surface of the eye covering 110 and the user's face) can define a variable volume. For example, the breathing module can include a second actuator 140 configured to vary the internal volume of the manifold 122. In this example, the controller 150 can sample the $CO_2$ concentration sensor and can increase the size of the flow control module 120 via the second actuator 140 if the measured $CO_2$ concentration of exhaled air is less than the threshold $CO_2$ concentration or falls outside of the target range of $CO_2$ concentrations, thereby increasing a volume of exhaled air—exhibiting a higher concentration of $CO_2$—contained within the flow control module 120 (or within the volume between the interior surface of the eye covering 110 and the user's face) following completion of an exhalation by the user. When the user breathes in during a next inhalation, the user can evacuate higher-$CO_2$-concentration air from the flow control module 120 and then fresh, lower-$CO_2$-concentration air from ambient, which may culminate in an elevated aggregate $CO_2$ concentration within the user's lung upon completion of the inhalation.

The controller 150 can thus modify the flow control module 120, the outlet port 126 or outlet pressure relief valve, or the eye covering 110, etc. to control a total concentration of $CO_2$ inhaled by the user, thereby stimulating the user's respiratory system and reducing a time before the user falls asleep and/or to increasing the user's total length of sleep during a sleep period. However, the controller 150 can modify the flow control module 120, the outlet port 126 or outlet pressure relief valve, or the eye covering 110, etc. in any other way. The breathing mask 100 can also include sensors—such as an $SPO_2$ or heart rate sensor—and the controller 150 can implement similar methods and techniques to selectively control an inspired $CO_2$ concentration based on signals read from these sensors or based on a wakefulness of the user, as described above.

In yet another implementation, the breathing mask 100 includes a set of interchangeable flow control modules, each defining a unique internal (or "dead") volume and configured to install over the nose region of the eye covering 110 to enable a user to reconfigure the breathing mask 100 for his breathing needs. For example, the breathing mask 100 can include: a first flow control module 120, as described above, defining a first internal volume; and a second flow control module similarly defining a second manifold, comprising a second nostril junction fluidly coupled to the second manifold and configured to mate with nostrils of the nose of the user, and comprising a second outlet port fluidly coupled to the second manifold but defining a second internal volume greater than the first internal volume. In this example, the first flow control module 120 and the second flow control module can be interchangeable over the nose region of the eye covering, and the breathing mask 100 can be provided to a user in kit form, including the eye covering 110, a set of flow control modules, the inlet check valve 130, the actuator 140, and the controller 150. The user may then assemble the breathing mask 100 with a particular flow control module that defines an internal volume matched to the user's particular characteristics or breathing needs. For example, first user with snoring complications may install a flow control module characterized by the smallest internal volume in the kit in order to achieve a highest $O_2$ concentration of air breathed by this user, which may be better suited to this user who may also be subject to sleep apnea complications. However, another user experiencing difficulty falling asleep may install a flow control module characterized by the largest internal volume in the kit; when this user exhales while wearing the breathing mask 100, this larger internal volume may fill with exhaled air that exhibits a $CO_2$ concentration greater than ambient. When the user subsequently inhales, air trapped in the flow control module may enter the user's lungs, followed by ambient air; the combination of exhaled and ambient air may thus entering this user's lungs thus exhibit a (slightly) greater $CO_2$ concentration than ambient air, which may increase sleepiness for the user and thus assist the user in falling asleep. However, in this implementation, the breathing mask 100 can include any other size and number of flow control modules, and a user may interchange these flow control modules in order to customize the breathing mask 100 to address any other one or more breathing needs.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A breathing mask comprising:
    an eye covering comprising an opaque material, defining an eye region configured to extend over both eyes of a user wearing the eye covering, and defining a nose region configured to extend over a nose of the user;
    a strap configured to retain the eye covering on a head of the user with the eye region over both eyes of the user and with the nose region aligned to the nose of the user;
    a flow control module coupled to the nose region of the eye covering, defining a manifold, comprising a nostril junction fluidly coupled to the manifold and configured to mate with nostrils of the nose of the user, and comprising an outlet port fluidly coupled to the manifold;

an inlet check valve fluidly coupled to the manifold and configured to open in response to a decrease in air pressure inside the manifold;

an actuator operable over a range of positions between a minimum-restriction position and a maximum-restriction position, the actuator minimally restricting airflow out of the outlet port in the minimum-restriction position and maximally restricting airflow out of the outlet port in the maximum-restriction position; and a controller configured to:
  trigger the actuator to transition from the minimum-restriction position toward the maximum-restriction position in response to transition of the user from a wakeful state to a sleep state;
  store a preset sleep delay duration approximating a common duration of transition from a wakeful state to a sleep state for users;
  initiate a timer for the sleep delay duration in response to activation of the breathing mask; and
  trigger the actuator to transition from the minimum-restriction position to an initial restriction position between the minimum-restriction position and the maximum-restriction position in response to conclusion of the timer.

2. The breathing mask of claim 1:
wherein the flow control module defines a first internal volume;
further comprising a second flow control module defining a second manifold, comprising a second nostril junction fluidly coupled to the second manifold and configured to mate with nostrils of the nose of the user, comprising a second outlet port fluidly coupled to the second manifold, and defining a second internal volume greater than the first internal volume; and
wherein the flow control module and the second flow control module are interchangeable over the nose region of the eye covering.

3. The breathing mask of claim 1, further comprising a wireless communication module configured to receive, from an external computing device associated with the user, the sleep delay duration customized by the user at the external computing device and the initial restriction position.

4. The breathing mask of claim 1:
wherein a wireless communication module further receives from the external computing device an indicator of upcoming activation of a wake alarm, set by the user, at the external computing device; and
wherein the controller is further configured to trigger the actuator to transition back to the minimum-restriction position at a time preceding upcoming activation of the wake alarm by a preset duration.

5. The breathing mask of claim 1:
further comprising a motion sensor electrically coupled to the controller; and
wherein the controller is configured to initiate the timer for the sleep delay duration in response to an output of the motion sensor indicating manipulation of the breathing mask in preparation for use by the user.

6. The breathing mask of claim 1:
wherein the eye covering defines a sleep mask and comprises an opaque flexible member defining a convex section, extending across the eye region and the nose region, and configured to deform about a medial axis of the head of the user to conform around the face of the user; and
wherein the flow control module comprises an elastic material configured to deform around the bottom of the nose of the user to mate the nostril junction around perimeter of the external nares of the user.

7. The breathing mask of claim 1:
further comprising a shroud adjacent the outlet port; and
wherein the actuator is coupled to the shroud and configured to:
  retract the shroud from the outlet port into the minimum-restriction position; and
  advance the shroud across the outlet port into the maximum-restriction position.

8. The breathing mask of claim 1:
wherein the outlet port comprises a tube of an elastic material extending downward from the manifold;
wherein the actuator comprises:
  a drawbar defining a hook looped around the tube of the outlet port; and
  an electromechanical actuator coupled to the drawbar opposite the hook and configured to:
    retract the drawbar to crush the tube of the outlet port to restrict airflow through the outlet port in the maximum-restriction position; and
    advance the drawbar to release the tube of the outlet port to permit airflow through the outlet port in the minimum-restriction position.

9. The breathing mask of claim 1:
further comprising a pressure relief valve arranged across the outlet port and configured to open in response to an air pressure inside the manifold exceeding a trigger pressure; and
wherein the actuator is coupled to the pressure relief valve and is configured to:
  set the trigger pressure of the pressure relief valve at a minimum pressure in the minimum-restriction position; and
  set the trigger pressure of the pressure relief valve at a maximum pressure in the maximum-restriction position.

10. A breathing mask comprising:
an eye covering comprising an opaque material, defining an eye region configured to extend over both eyes of a user wearing the eye covering, and defining a nose region configured to extend over a nose of the user;
a strap configured to retain the eye covering on a head of the user with the eye region over both eyes of the user and with the nose region aligned to the nose of the user;
a flow control module coupled to the nose region of the eye covering, defining a manifold, comprising a nostril junction fluidly coupled to the manifold and configured to mate with nostrils of the nose of the user, and comprising an outlet port fluidly coupled to the manifold;
a shroud adjacent the outlet port;
an inlet check valve fluidly coupled to the manifold and configured to open in response to a decrease in air pressure inside the manifold;
an actuator:
  coupled to the shroud;
  operable over a range of positions between a minimum-restriction position and a maximum-restriction position;
  configured to retract the shroud from the outlet port to minimally-restrict airflow out of the outlet port in the minimum-restriction position; and
  configured to advance the shroud across the outlet port to maximally-restrict airflow out of the outlet port in the maximum-restriction position; and a controller configured to trigger the actuator to transition from the minimum-restriction position toward the maximum-restriction position in response to transition of the user from a wakeful state to a sleep state.

11. A breathing mask comprising:
    an eye covering comprising an opaque material, defining an eye region configured to extend over both eyes of a user wearing the eye covering, and defining a nose region configured to extend over a nose of the user;
    a strap configured to retain the eye covering on a head of the user with the eye region over both eyes of the user and with the nose region aligned to the nose of the user;
    a flow control module:
        coupled to the nose region of the eye covering;
        defining a manifold;
        comprising a nostril junction fluidly coupled to the manifold and configured to mate with nostrils of the nose of the user; and
        comprising an outlet port fluidly coupled to the manifold and comprising a tube of an elastic material extending downward from the manifold;
    an inlet check valve fluidly coupled to the manifold and configured to open in response to a decrease in air pressure inside the manifold;
    an actuator:
        operable over a range of positions between a minimum-restriction position and a maximum-restriction position;
        comprising a drawbar defining a hook looped around the tube of the outlet port; and
        comprising an electromechanical actuator coupled to the drawbar opposite the hook and configured to:
            retract the drawbar to crush the tube of the outlet port to maximally-restrict airflow through the outlet port in the maximum-restriction position; and
            advance the drawbar to release the tube of the outlet port to minimally restrict airflow through the outlet port in the minimum-restriction position; and
    a controller configured to trigger the actuator to transition from the minimum-restriction position toward the maximum-restriction position in response to transition of the user from a wakeful state to a sleep state.

12. A breathing mask comprising:
    an eye covering comprising an opaque material, defining an eye region configured to extend over both eyes of a user wearing the eye covering, and defining a nose region configured to extend over a nose of the user;
    a strap configured to retain the eye covering on a head of the user with the eye region over both eyes of the user and with the nose region aligned to the nose of the user;
    a flow control module coupled to the nose region of the eye covering, defining a manifold, comprising a nostril junction fluidly coupled to the manifold and configured to mate with nostrils of the nose of the user, and comprising an outlet port fluidly coupled to the manifold;
    an inlet check valve fluidly coupled to the manifold and configured to open in response to a decrease in air pressure inside the manifold;
    a pressure relief valve arranged across the outlet port and configured to open in response to an air pressure inside the manifold exceeding a trigger pressure;
    an actuator:
        coupled to the pressure relief valve;
        operable over a range of positions between a minimum-restriction position and a maximum-restriction position;
        configured to set the trigger pressure of the pressure relief valve at a minimum pressure to minimally restrict airflow out of the outlet port in the minimum-restriction position; and
        configured to set the trigger pressure of the pressure relief valve at a maximum pressure to maximally restrict airflow out of the outlet port in the maximum-restriction position; and
    a controller configured to trigger the actuator to transition from the minimum-restriction position toward the maximum-restriction position in response to transition of the user from a wakeful state to a sleep state.

13. A breathing mask comprising:
    an eye covering comprising an opaque material, defining an eye region configured to extend over both eyes of a user wearing the eye covering, and defining a nose region configured to extend over a nose of the user;
    a strap configured to retain the eye covering on a head of the user with the eye region over both eyes of the user and with the nose region aligned to the nose of the user;
    a flow control module coupled to the nose region of the eye covering, defining a manifold, comprising a nostril junction fluidly coupled to the manifold and configured to mate with nostrils of the nose of the user, and comprising an outlet port fluidly coupled to the manifold;
    an inlet check valve fluidly coupled to the manifold and configured to open in response to a decrease in air pressure inside the manifold;
    an actuator operable over a range of positions between a minimum-restriction position and a maximum-restriction position, the actuator minimally restricting airflow out of the outlet port in the minimum-restriction position and maximally restricting airflow out of the outlet port in the maximum-restriction position;
    a biometric sensor arranged on the eye covering; and
    a controller configured to:
        trigger the actuator to transition from the minimum-restriction position toward the maximum-restriction position in response to transition of the user from a wakeful state to a sleep state;
        read outputs of the biometric sensor;
        interpret a first change in an output of the biometric sensor over a first period of time as transition of the user from the wakeful state to the sleep state over the first period of time;
        trigger the actuator to transition from the minimum-restriction position toward the maximum-restriction position over a first transition period succeeding the first period of time in response to detecting transition of the user from the wakeful state to the sleep state;
        interpret a second change in the output of the biometric sensor over a second time succeeding the first period of time as transition of the user from the sleep state to the wakeful state over the second period of time; and
        trigger the actuator to transition back to the minimum-restriction position over a second transition period in response to detecting transition of the user from the sleep state to the wakeful state.

14. A breathing mask comprising:
    an eye covering:
        defining a sleep mask comprising an eye region configured to extend over both eyes of a user wearing the eye covering and defining a nose region configured to extend over a nose of the user; and comprising an opaque flexible member defining a convex section, extending across the eye region and the nose region, and configured to deform about a medial axis of the head of the user to conform around the face of the user; and a strap configured to retain the eye covering on a head of the user with the eye region over both eyes of the user and with the nose region aligned to the nose of the user;

a flow control module:
- coupled to the nose region of the eye covering;
- defining a manifold;
- comprising a nostril junction fluidly coupled to the manifold and configured to mate with nostrils of the nose of the user;
- comprising an outlet port fluidly coupled to the manifold; and
- comprising an elastic material configured to deform around the bottom of the nose of the user to mate the nostril junction around perimeter of the external nares of the user an inlet check valve fluidly coupled to the manifold and configured to open in response to a decrease in air pressure inside the manifold;

an actuator operable over a range of positions between a minimum-restriction position and a maximum-restriction position, the actuator minimally restricting airflow out of the outlet port in the minimum-restriction position and maximally restricting airflow out of the outlet port in the maximum-restriction position; and a controller configured to trigger the actuator to transition from the minimum-restriction position toward the maximum-restriction position in response to transition of the user from a wakeful state to a sleep state.

15. The breathing mask of claim 14:

further comprising a set of textile cushions arranged about a perimeter of the eye covering, configured to offset the opaque flexible member from the face of the user, and configured to ventrally align the nostril junction to nostrils of the user; and wherein the actuator and the flow control module are fully contained within the perimeter of the eye covering.

16. The breathing mask of claim 14:

further comprising a battery arranged in a first rigid housing located on a first lateral side of the flow control module;

wherein the actuator is arranged in a second rigid housing located on a second lateral side of the flow control module; and further comprising a beam mounted to the eye covering, extending across the flow control module, coupling the first rigid housing to the second rigid housing, and configured to preferentially deflect with the eye covering about the medial axis of the head of the user.

17. The breathing mask of claim 16:

wherein the eye covering comprises molded foam;
wherein the beam comprises a rigid polymer;
wherein the flow control module comprises an elastic silicone body;
wherein the outlet port comprises an elastic silicone tube physically coextensive with the elastic silicone body; and
wherein the beam defines a bore configured to accept and retain the elastic silicone tube to flexibly couple the elastic silicone body to the eye covering.

18. A breathing mask comprising:

an eye covering comprising an opaque material, defining an eye region configured to extend over both eyes of a user wearing the eye covering, and defining a nose region configured to extend over a nose of the user;

a strap configured to retain the eye covering on a head of the user with the eye region over both eyes of the user and with the nose region aligned to the nose of the user;

a flow control module coupled to the nose region of the eye covering, defining a manifold, comprising a nostril junction fluidly coupled to the manifold and configured to mate with nostrils of the nose of the user, and comprising an outlet port fluidly coupled to the manifold;

an inlet check valve fluidly coupled to the manifold and configured to open in response to a decrease in air pressure inside the manifold;

an actuator operable over a range of positions between a minimum-restriction position and a maximum-restriction position, the actuator minimally restricting airflow out of the outlet port in the minimum-restriction position and maximally restricting airflow out of the outlet port in the maximum-restriction position; and a controller configured to:
- trigger the actuator to transition from the minimum-restriction position toward the maximum-restriction position in response to transition of the user from a wakeful state to a sleep state;
- read a first output of a microphone at a first time;
- trigger the actuator to move from its current position to a first position in response to characterizing the first output of the microphone as snoring by the user, the first position defined between the current position and the maximum-restriction position and associated with a first degree of obstruction to airflow through the outlet port;
- read a second output of the microphone at a second time succeeding the first time by a preset buffer time; and
- trigger the actuator to move from the first position to a second position in response to characterizing the second output of the microphone as snoring by the user, the second position defined between the first position and the maximum-restriction position and associated with a second degree of obstruction to airflow through the outlet port greater than the first degree of obstruction.

19. The breathing mask of claim 18:

further comprising a wireless communication module coupled to the eye covering and electrically coupled to the actuator;

wherein the controller comprises a software program executing on an external computing device and configured to communicate with the actuator via the wireless communication module.

20. The breathing mask of claim 18:

further comprising:
- a buzzer coupled to the eye covering; and
- a position sensor configured to output a signal corresponding to an orientation of the eye covering;

wherein the controller is further configured to, in response to an output of the position sensor indicating an orientation of the eye covering that is associated with snoring:
- trigger the actuator to move to the minimum-restriction position; and
- actuate the buzzer to wake the user.

* * * * *